US009493846B2

(12) United States Patent
Ding et al.

(10) Patent No.: US 9,493,846 B2
(45) Date of Patent: Nov. 15, 2016

(54) VIRUS DISCOVERY BY SEQUENCING AND ASSEMBLY OF VIRUS-DERIVED SIRNAS, MIRNAS, PIRNAS

(75) Inventors: Shou-Wei Ding, Riverside, CA (US); Qingfa Wu, Riverside, CA (US)

(73) Assignee: The Regents of the University of California, Oakland, CA (US)

( * ) Notice: Subject to any disclaimer, the term of this patent is extended or adjusted under 35 U.S.C. 154(b) by 140 days.

(21) Appl. No.: 13/375,467

(22) PCT Filed: Jun. 1, 2010

(86) PCT No.: PCT/US2010/036849
§ 371 (c)(1),
(2), (4) Date: Mar. 20, 2012

(87) PCT Pub. No.: WO2010/141433
PCT Pub. Date: Dec. 9, 2010

(65) Prior Publication Data
US 2012/0172237 A1    Jul. 5, 2012

Related U.S. Application Data

(60) Provisional application No. 61/183,377, filed on Jun. 2, 2009, provisional application No. 61/286,742, filed on Dec. 15, 2009.

(51) Int. Cl.
C12Q 1/68      (2006.01)
C12Q 1/70      (2006.01)
G06F 19/22     (2011.01)
G06F 19/14     (2011.01)

(52) U.S. Cl.
CPC .............. C12Q 1/70 (2013.01); G06F 19/22 (2013.01); *C12Q 2600/178* (2013.01); *G06F 19/14* (2013.01)

(58) Field of Classification Search
None
See application file for complete search history.

(56) References Cited

U.S. PATENT DOCUMENTS

| | | | | |
|---|---|---|---|---|
| 8,546,553 B2* | 10/2013 | Terns et al. | .................. | 536/24.5 |
| 2007/0111227 A1* | 5/2007 | Green et al. | ...................... | 435/6 |
| 2008/0115240 A1* | 5/2008 | Aukerman et al. | ........... | 800/278 |
| 2009/0265811 A1* | 10/2009 | Stonaker et al. | ............. | 800/286 |
| 2011/0160290 A1* | 6/2011 | Tewari | ........................ | 514/44 R |

OTHER PUBLICATIONS

Kreuze et al "Complete viral genome sequence and discovery of novel viruses by deep sequencing of small RNAs: a generic method of diagnosis, discovery and sequencing of viruses" Virology, May 25, 2009, vol. 388, No. 1, pp. 1-7).*
Li et al "Improved rapid amplification of cDNA ends (RACE) for mapping both the 5' and 3' terminal sequences of paramyxovirus genomes" (J Virol Methods, Dec. 2005: vol. 130, No. 1-2, pp. 154-156).*
Donaire et al in "Deep-sequencing of plant viral small RNAs reveals effective and widespread targeting of viral genomes" (Virology: vol. 392: pp. 203-214, published online Aug. 7, 2009).*
Qi et al in "Small RNA Deep Sequencing Reveals Role for Arabidopsis thaliana RNA-Dependent RNA Polymerases in Viral siRNA Biogenesis" (PLoS One: vol. 4, Issue 3: e4971, pp. 1-11, published Mar. 24, 2009).*
Al Rwahnih et al in "Deep sequencing analysis of RNAs from a grapevine showing Syrah decline symptoms reveals a multiple virus infection that includes a novel virus" (Virology: vol. 387, pp. 395-401, published Feb. 28, 2009; entire document).*
Ding & Voinnet entitled "Antiviral immunity directed by small RNAs" (Cell 2007 vol. 130, pp. 413-426).*
Brennecke et al in "Discrete Small RNA-Generating Loci as master Regulators of Transposon Activity in *Drosophila*" (Cell vol. 128, pp. 1089-1103, published Mar. 23, 2007).*
Kreuze, J.F. et al., "Complete viral genome sequence and discovery of novel vi ruses by deep sequencing of small RNAs: a generic method for diagnosis, disc overy and sequencing of viruses", Virology, May 25, 2009, vol. 368, No. 1, pp. 1-17.
Li Z. et al., "Improved rapid amplification of cDNA ends (RACE) for mapping both the 5' and 3' terminal sequences of paramyxovirus genomes", J. Virol Methods, Dec. 2005, vol. 130, No. 1-2, pp. 154-156.
Nickitas-Etienne, Athina, International Preliminary Examination Report, PCT/US2010/036849, The International Bureau of WIPO, Dec. 6, 2011.
Park, Jung Min, International Search Report and Written Opinion, PCT/US2010/036849, Korean Intellectual Property Office, Feb. 21, 2011.
Wu Q. et al., "Virus discovery by deep sequencing and assembly of virus-derived small silencing RNAs", Proc. Natl. Acad. Sci. USA, Jan. 26, 2010, vol. 107, No. 4, pp. 1606-1611.
Zerbino D.R. et al., "Velvet: algorithms for de novo short read assembly using de Brui jn graphs" May 2008, vol. 18, No. 5, pp. 821-829.

\* cited by examiner

*Primary Examiner* — Catherine S Hibbert
(74) *Attorney, Agent, or Firm* — Joseph R. Baker, Jr.; Gavrilovich, Dodd & Lindsey LLP

(57) ABSTRACT

In one embodiment, the disclosure provides methods and systems for identifying viral nucleic acids in a sample. In another embodiment the invention provides methods for viral genome assembly and viral discovery using small inhibitory RNAs, or "small silencing," RNAs (siRNAS), micro-RNAs (miRNAs) and/or PIWI-interacting RNAs (piRNAs), including siRNAS, miRNAs and/or piRNAs isolated or sequenced from invertebrate organisms such as insects (*Anthropoda*), nematodes (*Nemapoda*), *Mollusca, Porifera*, and other invertebrates, and/or plants, fungi or algae, *Cyanobacteria* and the like.

15 Claims, 8 Drawing Sheets

VIRUS DISCOVERY BY SEQUENCING AND ASSEMBLY OF VIRUS-DERIVED SIRNAS, MIRNAS, PIRNAS

RELATED APPLICATIONS

This application is a national phase application claiming benefit of priority under 35 U.S.C. §371 to Patent Convention Treaty (PCT) International Application Serial No: PCT/US2010/036849, filed Jun. 1, 2010, which claims benefit of priority to U.S. Provisional Patent Application Ser. No. ("USSN") 61/183,377, filed Jun. 2, 2009, and U.S. Ser. No. 61/286,742, filed Dec. 15, 2009. The aforementioned applications are expressly incorporated herein by reference in their entirety and for all purposes.

STATEMENT AS TO FEDERALLY SPONSORED RESEARCH

This invention was made with government support under Grant No. AI052447 awarded by the National Institutes of Health (NIH) and Grant No. 2007-35319-18325 awarded by the USDA. The government has certain rights in the invention.

TECHNICAL FIELD

In one embodiment, the disclosure provides methods and systems for identifying viral nucleic acids in a sample. In another embodiment the invention provides methods for viral genome assembly and viral discovery using small inhibitory RNAs, or "small silencing," RNAs (siRNAS), micro-RNAs (miRNAs) and/or PIWI-interacting RNAs (piRNAs), including siRNAS, miRNAs and/or piRNAs isolated or sequenced from invertebrate organisms such as insects (*Anthropoda*), nematodes (*Nemapoda*), *Mollusca, Porifera*, and other invertebrates, and/or plants, fungi or algae, *Cyanobacteria* and the like.

BACKGROUND

Discovery of new viruses is often hindered by difficulties in their amplification in cell culture and/or lack of their cross-reactivity in serological and nucleic acid hybridization assays to known viruses. Many new viruses have been recently identified in environmental and clinical samples using metagenomic approaches, in which viral particles are first purified and viral nucleic acid sequences are then randomly amplified prior to subcloning and sequencing (Delwart, 2007).

The Dicer family of host immune receptors mediates antiviral immunity in fungi, plants and invertebrate animals by RNA interference (RNAi) or RNA silencing (1-3). In this immunity, a viral double-stranded RNA (dsRNA) is recognized by Dicer and diced into small interfering RNAs (siRNAs). These virus-derived siRNAs are then loaded into an RNA silencing complex to act as specificity determinants and to guide slicing of the target viral RNAs by an Argonaute protein (AGO) present in the complex. Dicer proteins typically contain an RNA helicase domain, a PAZ domain shared with AGOs, and two tandem type III endoribonuclease (RNase III) domains. Dicer cleaves dsRNA with a simple preference toward a terminus of dsRNA, producing duplex small RNA fragments of discrete sizes progressively from the terminus (4).

In addition to siRNAs, microRNAs (miRNAs) and PIWI-interacting RNAs (piRNAs) also guide RNA silencing in similar complexes but with distinct AGOs (4-6). In *Drosophila melanogaster*, miRNAs and siRNAs are predominantly 22 and 21 nucleotides in length, dependent on Dicer-1 (DCR1) and DCR2 for their biogenesis, and act in silencing complexes containing AGO1 and AGO2 in the AGO subfamily, respectively (4-6). In contrast, ~24-30-nt piRNAs are Dicer-independent and require AGO3, Aubergine (AUB) and PIWI in the PIWI subfamily for their biogenesis (4-6). Genetic analyses (7-10) have clearly demonstrated a role for *D. melanogaster* DCR2 in the immunity and biogenesis of viral siRNAs targeting diverse positive-strand (+) RNA viruses, including Flock house virus (FHV), cricket paralysis virus, *Drosophila* C virus (DCV), and Sindbis virus (SINV). Cloning and sequencing of small RNAs from FHV-infected *Drosophila* cells further indicate that the viral dsRNA replicative intermediates (vRI-dsRNA) are the substrate of DCR2 and the precursor of viral siRNAs (11-12). *Drosophila* susceptibility to *Drosophila* X virus (DXV), which contains a dsRNA genome, is influenced by components from both the siRNA (e.g., AGO2 & R2D2) and piRNA (e.g., AUB & PIWI) pathways (13). However, detection of small RNAs derived from any dsRNA virus has not been reported yet (1, 13).

Virus-derived small RNAs were first detected in plants infected with a +RNA virus (14). The Dicer proteins involved in the production of siRNAs targeting both +RNA viruses and DNA viruses have been identified in *Arabidopsis thaliana* (2-3), which encode AGOs in the AGO subfamily but not in the PIWI subfamily (15). Cloning and sequencing of plant viral siRNAs suggest that they may be processed either from vRI-dsRNA or hairpin regions of single-stranded RNA precursors (16-20). Production of viral siRNAs has also been demonstrated in fungi, silkworms, mosquitoes, and nematodes in response to infection with +RNA viruses and viral small silencing RNAs produced in fungi and mosquitoes have recently been cloned and sequenced (21-25).

The available data thus illustrate that accumulation of virus-derived small silencing RNAs is a common feature of an active immune response to viral infection in diverse eukaryotic host species.

SUMMARY

The disclosure provides a method for viral discovery that is independent of either amplification or purification of viral particles. Many human diseases such as approximately half of all analyzed cases of human encephalitis and gastroenteritis, have no identified etiology. Thus, discovery of new viruses should facilitate identification of human pathogenic viruses, improve the understanding of their transmission and provide diagnostic tools and targets for the development of anti-virals.

The disclosure provides methods of identifying viral nucleic acid, assembling viral genomes and discovering viruses based upon the mechanism of invertebrate, plant, algae, fungal etc. processing of viral small inhibitory RNAs, or "small silencing," RNAs (siRNAS), micro-RNAs (miRNAs) and/or PIWI-interacting RNAs (piRNAs), including miRNA-, piRNA-, siRNA and/or RNAi-mediated viral immunity in plants and invertebrates, including insects (*Drosophila melanogaster* and mosquitoes) and nematodes (*Caenorhabditis elegans*), and algae, fungus, *Cyanobacteria* and the like.

In alternative embodiments, the invention provides methods comprising:

(a) (i) obtaining a plurality of naturally occurring 18-28 nucleotide RNA fragments, or siRNAs, or miRNAs and/or piRNAs, to generate an RNA library, or, obtaining a plurality of 18-28 nucleotide RNA fragments, or siRNAs, or miRNAs and/or piRNAs from an organism or organisms, or a plant or plants; and (ii) determining the sequence of the RNA fragments, or siRNAs, or miRNAs and/or piRNAs, and using those sequences to assemble the RNA fragments, or siRNAs, or miRNAs and/or piRNAs into at least one contiguous unit ("a contig") comprising a plurality of the nucleotide RNA fragments siRNAs, miRNAs and/or piRNAs; or (b) the method of (a), wherein the contigs are assembled using the help of a computer program, wherein optionally the computer program is VELVET.

In alternative embodiments, the methods further comprise determining the sequence of the assembled contiguous unit, or the contig; or further comprise:

(a) searching a database of viral or microorganism sequences using the at least one contiguous sequence to identify a viral or microorganism genome, nucleic acid or protein-encoding sequence, or subsequence thereof, having significant homology to the assembled contiguous unit; or (b) the method of (a), wherein the database comprises non-redundant nucleotide sequences; or (c) the method of (a), wherein the database comprises in silico translation sequences.

wherein optionally the assembled contig sequence has significant homology to a known viral genus or genome.

In alternative embodiments, the methods further comprise searching a database of viral or microorganism sequences using the at least one contiguous sequence to identify a viral or microorganism genome, nucleic acid or protein-encoding sequence, or subsequence thereof, having at least about 50% to about 100% percent homology to all or part of the assembled contiguous sequence.

In alternative embodiments, the methods further comprise making a phylogenetic analysis of the identified viral or microorganism genome, nucleic acid or protein-encoding sequence with the contiguous sequence.

In alternative embodiments, the methods further comprise identifying and annotating the phylogenetic analysis of the identified viral sequence with the contiguous sequence.

In alternative embodiments, the obtained RNA or nucleotide sequences are substantially purified or isolated from an organism of interest.

In alternative embodiments, the methods further comprise substantially purifying small RNA fragments, or siRNAs, or miRNAs and/or piRNAs, from an organism of interest and sequencing the RNA fragments to obtain an RNA library.

In alternative embodiments, the methods further comprise removing sequenced segments from the library that overlap with the genomic sequence of the organism of interest from which the RNA was derived.

In alternative embodiments, the methods further comprise filling in gaps between the contiguous sequences. In one embodiment, filling in the gaps between the contiguous sequences comprises use of RT-PCR and/or sequencing to fill in gaps between the contiguous sequences.

In alternative embodiments, the methods further comprise completing a genomic sequence of a virus or a microorganism comprising the contiguous sequence using 5'-RACE and 3'-RACE.

In one embodiment, the organism or organisms is/are an invertebrate, an insect (*Anthropoda*), a nematode (*Nemapoda*), a *Mollusca*, a *Porifera*, a plant, a fungi, an algae, a *Cyanobacteria*; or the organism or organisms are identified or unidentified and are derived from an environmental sample. In one embodiment, the environmental sample is a soil sample, a water sample or an air sample.

In one embodiment, the invention provides methods for identifying a virus, comprising:

constructing a small RNA library from an organism or organisms;

deep sequencing the small RNA library;

assembling the sequenced small RNAs using (a) all of the sequenced small RNAs of 18-28 nucleotides in length, or siRNAs, or miRNAs and/or piRNAs; or (b) small RNAs, or siRNAs, or miRNAs and/or piRNAs, of a defined length into a plurality of contigs;

identifying and removing those assembled sequences mapped onto the genome of the organism to provide an enriched set of contigs;

performing a homology search of contigs against known viruses at both the nucleotide and protein levels;

optionally using RT-PCR and sequencing to fill the gaps between the contigs that show limited similarities with a known virus;

completing the full-length genomic sequence of the identified virus with 5'-RACE and 3'-RACE; and annotating the identified virus.

In one embodiment, the organism or organisms is/are an invertebrate, an insect (*Anthropoda*), a nematode (*Nemapoda*), a *Mollusca*, a *Porifera*, a plant, a fungi, an algae, a *Cyanobacteria*; or the organism or organisms are identified or unidentified and are derived from an environmental sample. In one embodiment, the environmental sample is a soil sample, a water sample or an air sample.

The details of one or more embodiments of the disclosure are set forth in the accompanying drawings and the description below. Other features, objects, and advantages of the disclosure will be apparent from the description and drawings, and from the claims.

All publications mentioned herein are incorporated herein by reference in full for the purpose of describing and disclosing the methodologies, which are described in the publications, which might be used in connection with the description herein. The publications discussed above and throughout the text are provided solely for their disclosure prior to the filing date of the present application. Nothing herein is to be construed as an admission that the inventors are not entitled to antedate such disclosure by virtue of prior disclosure.

DESCRIPTION OF DRAWINGS

FIG. 7A illustrates DTV, DBV, DXV and ANV were all detected by RT-PCR in non-contaminated S2 cells 4 days after inoculation with the supernatant of the S2-GMR cells; FIG. 7B illustrates detection of a DI-RNA derived from ANV RNA2 in S2-GMR cells (right lane) and in S2 after inoculation with the supernatant of S2-GMR cells (left lane) by Northern blot hybridizations using a probe recognizing the 3'-terminal 120 nt of RNA2; FIG. 7C illustrates structure of the cloned DI-RNA of ANV (top) and mapping of the perfect-matched 21-nt siRNAs sequenced from S2-GMR cells to the positive (blue) and negative (red) strands of ANV RNA2 (20-nt windows) (bottom); as discussed in detail in Example 2, below.

Like reference symbols in the various drawings indicate like elements.

DETAILED DESCRIPTION

Figure 1:
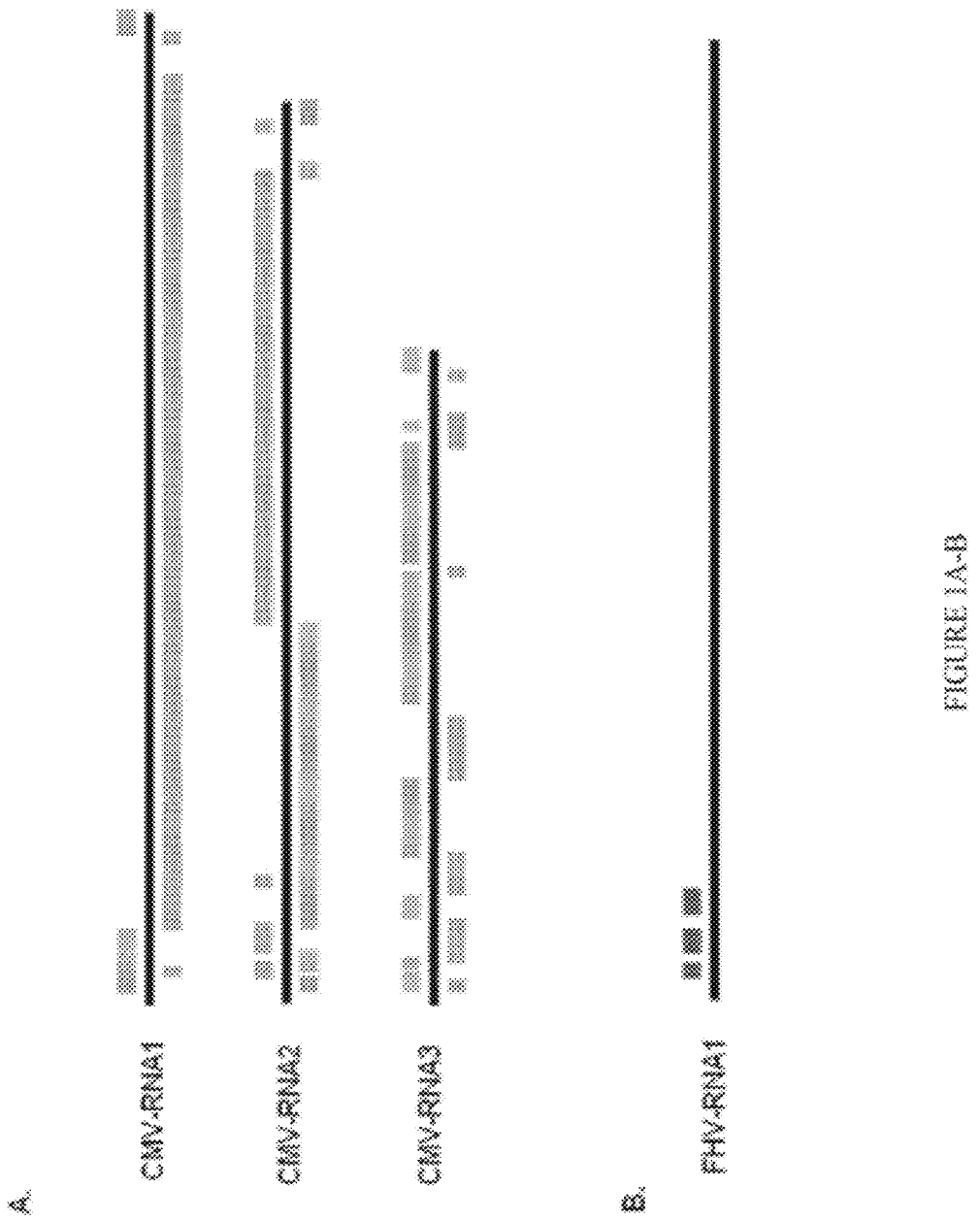
FIG. 1A and Figure B shows distribution of assembled viral siRNA contigs on the tripartite and bipartite RNA genome of (a) CMV and (b) FHV; as discussed in detail in Example 1, below.

In alternative embodiments the invention provides methods for viral genome assembly and viral discovery using small inhibitory RNAs, or "small silencing," RNAs (siRNAS), micro-RNAs (miRNAs) and/or PIWI-interacting RNAs (piRNAs), including siRNAS, miRNAs and/or piRNAs isolated or sequenced from invertebrate organisms such as insects (*Anthropoda*), nematodes (*Nemapoda*), *Mollusca*, *Porifera*, and other invertebrates, and/or plants, fungi or algae, *Cyanobacteria* and the like.

As described in Example 2, we found that viral small silencing RNAs produced by invertebrate animals are overlapping in sequence and can assemble into long contiguous fragments of the invading viral genome from small RNA libraries sequenced by next generation platforms. Based on this finding, we developed an approach of virus discovery in invertebrates by deep sequencing and assembly of total small RNAs (vdSAR) isolated from a host organism of interest.

As described in Example 2, alternative embodiments of the invention revealed mix infection of *Drosophila* cell lines and adult mosquitoes by multiple RNA viruses, five of which were new. Analysis of small RNAs from mix infected *Drosophila* cells showed that infection of all three distinct dsRNA viruses triggered production of viral siRNAs with features similar to siRNAs derived from +RNA viruses. Our study also revealed production and assembly of virus-derived piRNAs in *Drosophila* cells, suggesting a novel function of piRNAs in viral immunity. Thus, unique features of the invention's vdSAR can discover new invertebrate and arthropod-borne animal and human viral pathogens.

As used herein and in the appended claims, the singular forms "a," "and," and "the" include plural referents unless the context clearly dictates otherwise. Thus, for example, reference to "an siRNA" includes a plurality of such siRNAs and reference to "the virus" includes reference to one or more viruses, and so forth.

Unless defined otherwise, all technical and scientific terms used herein have the same meaning as commonly understood to one of ordinary skill in the art to which this disclosure belongs. Although any methods and reagents similar or equivalent to those described herein can be used in the practice of the disclosed methods and compositions, the exemplary methods and materials are now described.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

The disclosure of U.S. Pat. No. 7,211,390, describing techniques associated with "deep sequencing" is incorporated herein by reference.

In immunity, viral infection induces production of virus-derived small interfering RNAs (siRNAs), pi-RNAs and miRNAs that subsequently guide specific viral RNA clearance by the RNA interference (RNAi), pi-RNA and miRNA mechanism. In *D. melanogaster*, for example, siRNAs of 21 nucleotides long targeting several positive-strand (+) RNA viruses are produced by Dicer-2 from processing dsRNA replicative intermediates synthesized during viral RNA replication. Assisted by the dsRNA-binding protein R2D2, these viral siRNAs are then loaded in Argonaute-2 to direct viral RNA clearance (Galiana-Arnoux et al., 2006; Wang et al., 2006; Zambon et al., 2006). As a counter defense, viruses encode essential pathogenesis proteins that are viral suppressors of RNAi (VSRs) (Li and Ding, 2006; Mlotshwa et al., 2008). VSRs may inhibit either the production or activity of viral siRNAs by targeting the dsRNA precursors, siRNAs or Argonaute proteins. Several nuclear-replicating DNA viruses produce virus-derived microRNAs following infection of their mammalian host cells and many proteins encoded by mammalian RNA and DNA viruses exhibit VSR activity. However, the current consensus is that in vertebrates viral dsRNA triggers PKR and interferon responses instead of the RNAi response.

The disclosure provides a method for virus discovery that is independent of either amplification or purification of viral particles. Many of the human diseases such as approximately half of all analyzed cases of human encephalitis and gastroenteritis, have no identified etiology. Thus, discovery of new viruses or the identification of the presence of viral infection can facilitate identification of human pathogenic viruses, improve our understanding of their transmission and provide diagnostic tools and targets for the development of anti-virals.

The disclosure is based, in part, on the understanding of the mechanism of RNAi-mediated, including pi-RNA-, miRNA- and siRNA-based, viral immunity. In this immunity, viral infection induces production of virus-derived small interfering RNAs (siRNAs), pi-RNAs and miRNAs, that subsequently guide specific viral RNA clearance by the RNA interference (RNAi) (pi-RNA-, miRNA- and siRNA-based) mechanism. In *D. melanogaster*, for example, siRNAs of 21 nucleotides long targeting several positive-strand (+) RNA viruses are produced by Dicer-2 from processing dsRNA replicative intermediates synthesized during viral RNA replication. Assisted by the dsRNA-binding protein R2D2, these viral siRNAs are then loaded in Argonaute-2 to direct viral RNA clearance (Galiana-Arnoux et al., 2006; Wang et al., 2006; Zambon et al., 2006). As a counter defense, viruses encode essential pathogenesis proteins that are viral suppressors of RNAi (VSRs) (Li and Ding, 2006; Mlotshwa et al., 2008). VSRs may inhibit either the production or activity of viral siRNAs, pi-RNAs and miRNAs by targeting the dsRNA precursors, siRNAs, pi-RNAs and miRNAs or Argonaute proteins. Several nuclear-replicating DNA viruses produce virus-derived microRNAs following infection of their mammalian host cells and many proteins encoded by mammalian RNA and DNA viruses exhibit VSR activity (Ding and Voinnet, 2007). However, the current consensus is that in vertebrates viral dsRNA triggers PKR and interferon responses instead of the RNAi (siRNAs, pi-RNAs and miRNAs) response.

The disclosure demonstrates by the next generation sequencing technologies viral siRNAs, pi-RNAs and miRNAs produced in plants and fruit flies infected with positive-strand RNA viruses, which are closely related to human pathogenic viruses such as poliovirus and West Nile virus. The results show that viral siRNAs produced by the host immune system in response to viral infection are overlapping in sequence and can be assembled back into long continuous fragments (contigs) of the infecting viral RNA genome using assembly programs developed for short read genome sequencing. Unlike individual siRNAs, pi-RNAs and miRNAs, the contigs assembled from viral siRNAs, pi-RNAs and miRNAs can be translated into protein sequences in silico for homology searches to identify new viruses that may be only distantly related to known viruses.

The disclosure demonstrates that deep sequencing by the next generation technologies and assembly of virus-derived siRNAs, pi-RNAs and miRNAs can be employed as a new approach for virus discovery and identification. Indeed, the examination of a recently sequenced small RNA library (Flynt et al., 2009) made from a *Drosophila* cell line found that the cell line is infected with at least five distinct RNA viruses. These include two known viruses and three new viruses belonging to different genera not previously described. Since virus infection of plants and invertebrates inevitably results in the production of virus-derived siRNAs, pi-RNAs and miRNAs, this invention does not depend on the ability to either amplify the virus or purify the viral particle to enrich viral nucleic acids, which is essential for the current technologies. Importantly, any viruses detected by the method of the disclosure are live and replication-competent because viral siRNAs, pi-RNAs and miRNAs are products of an active host immune response to viral infection.

The observation that individual viral siRNAs, pi-RNAs and miRNAs can be assembled back to longer genome fragments of the invading virus provides an exciting new method for virus discovery by deep sequencing and assembly of viral siRNAs, pi-RNAs and miRNAs. Unlike individual siRNAs, pi-RNAs and miRNAs, the contigs assembled from viral siRNAs, pi-RNAs and miRNAs can be translated into protein sequences in silico for homology searches to identify new viruses that may be distantly related to known viruses.

The disclosure provides a frame of the VDsiR comprised of bioinformatics analysis and experimental verification. Small RNA assembling is a useful component of the system, the number of input sequences and distinct programs have impact on the output. In a pilot study (described herein), Velvet was found to be a useful program for the project, which employs the principle of de Bruijn graphs to build up continuous sequence from short reads in short run time (Zerbino et al, 2008).

The disclosure thus provides in one embodiment, a method comprising (i) obtaining nucleotide sequences from a small RNA libraries comprising a plurality of naturally occurring 18-28 nucleotide RNA fragments to obtain a sequenced small RNA library; (ii) assembling the sequences in the sequenced small RNA library into at least one contiguous sequence comprising a plurality of nucleotide RNA fragment sequences; optionally filling in gaps in a sequence by RT-PCR techniques; (iii) searching a database of viral sequence using the at least one contiguous sequence to identify a viral sequence having at least 50%-100 percent homology to the contiguous sequence; (iv) identifying and annotating the phylogenetic analysis of the identified viral sequence with the contiguous sequence.

It will be understood that a sequence library may be provided by a third party or made available to a user by any number of ways (i.e., internet, computer readable medium and the like) and thus the process described above can be adapted to carry the process and identify or annotate a virus accordingly. In some embodiment, however, the library may be a sample library comprising substantially purified RNA from an organism of interest. In such instances, deep sequencing techniques are carried out and a sequence library created. In yet another embodiment, a sample comprising substantially purifying small RNA fragments from an organism of interest are provided in which case sequencing the RNA fragments to obtain the small RNA library is performed.

In yet another embodiment, if a gross RNA sample from an organism is provided or where increased homology searching is desired, the method may optionally include removing sequenced segments from the library that overlap with the genomic sequence of the organism of interest from which the RNA was derived.

In yet another embodiment, the method further comprises completing a genomic sequence of a virus comprising the contiguous sequence using 5'-RACE and 3'-RACE.

For example, the disclosure demonstrates in the specific embodiments and proof of principle that a method including the steps of construction of a small RNA library from cell culture or adults insects such as mosquitoes or fruit flies; deep sequencing of the small RNA libraries with an Illumina 2G ANALYSER™; assembly of the sequenced small RNAs by Velvet using either all of the sequenced small RNAs of 18-28 nucleotides in length or small RNAs of specific lengths such as 21-nt and 22-nt, which most likely represent the products of *Drosophila* Dicer-2 and Dicer-1, respectively, to generate a contig(s), contigs of virus-derived siRNAs may include features such as specific enrichment of 21- to 22-nt small RNAs, the presence of small RNAs of both polarities and the high density of siRNAs (number of siRNAs/length of contigs); identification and removal of those assembled sequences mapped onto the host genome when the genome sequence is known, which reduces the number of the candidates for next steps; homology search of contigs with known virus at both the nucleotide and protein levels; in an optional embodiment, RT-PCR and sequencing can be used to fill the gaps between the contigs that show limited similarities with a known virus; optionally completing the full-length genomic sequence of the identified virus with 5'-RACE and 3'-RACE; and annotation and phylogenetic analysis of the identified virus, resulted in the identification of 2 known viruses and 3 novel viruses from a *D. melanogaster* sample.

As used herein a sample is any sample that can contain a virus. Thus, the sample can be obtained from the environment, from a specific organism (including plants, insects and mammals). An environmental sample can be obtained from any number of sources (as described above), including, for example, insect feces, hot springs, soil and the like. Any source of nucleic acids in purified or non-purified form can be utilized as starting material. Thus, the nucleic acids may be obtained from any source which is contaminated by an infectious organism (e.g. a virus). The sample can be an extract from any bodily sample such as blood, urine, spinal fluid, tissue, vaginal swab, stool, amniotic fluid or buccal mouthwash from any mammalian organism. For non-mammalian (e.g., invertebrates) organisms the sample can be a tissue sample, salivary sample, fecal material or material in the digestive tract of the organism. For example, in horticulture and agricultural testing the sample can be a plant, soil, liquid or other horticultural or agricultural product; in food testing the sample can be fresh food or processed food (for example infant formula, seafood, fresh produce and packaged food); and in environmental testing the sample can be liquid, soil, sewage treatment, sludge and any other sample in the environment.

The sample can be processed using techniques known in the art for deep sequencing. In some embodiments, the sample is treated with an RNase inhibitor to prevent degradation of RNA oligonucleotides in the sample. RNase inhibitor and cocktails are known in the art and are commercially available.

Deep sequencing techniques are known in the art as described above and elsewhere herein. A sample comprising small RNA fragments either purified, substantially purified or non-purified, can be subjected to deep sequencing to sequence a large number of RNA fragments in the sample.

As described herein the sequences can then be aligned and matched so as to generate at least one, typically a plurality, of contigs comprising a plurality of overlapping and adjacent RNA fragments. Algorithms and computer programs to perform such matching and generating of contigs are known in the art (see, e.g., VELVET™: algorithms for de novo short read assembly using de Bruijn graphs. D. R. Zerbino and E. Birney. Genome Research 18:821-829; and information on the world-wide-web. The results from, for example, VELVET™ comprising longer contigs of between 30-50, 50-100 to several hundred bases can be used to screen nucleic acid sequence databases directly or may be translated to screen amino acid databases.

A number of source databases are available that contain either a nucleic acid sequence and/or a deduced amino acid sequence to identify or determine related sequences or homologs. All or a representative portion of the sequences can be used to search a sequence database (e.g., GenBank, PFAM or ProDom), either simultaneously or individually. A number of different methods of performing such sequence searches are known in the art. The databases can be specific for a particular organism or a collection of organisms. The sequence data is aligned to the sequences in the database or databases using algorithms designed to measure homology between two or more sequences.

Such sequence alignment methods include, for example, BLAST (Altschul et al., 1990), BLITZ (MPsrch) (Sturrock & Collins, 1993), and FASTA (Person & Lipman, 1988). The probe sequence (e.g., the sequence data from the clone) can be any length, and will be recognized as homologous based upon a threshold homology value. The threshold value may be predetermined, although this is not required. The threshold value can be based upon the particular polynucleotide length. To align sequences a number of different procedures can be used. Typically, Smith-Waterman or Needleman-Wunsch algorithms are used. However, as discussed faster procedures such as BLAST, FASTA, PSI-BLAST can be used.

For example, optimal alignment of sequences for aligning a comparison window may be conducted by the local homology algorithm of Smith (Smith and Waterman, Adv Appl Math, 1981; Smith and Waterman, J Teor Biol, 1981; Smith and Waterman, J Mol Biol, 1981; Smith et al, J Mol Evol, 1981), by the homology alignment algorithm of Needleman (Needleman and Wuncsch, 1970), by the search of similarity method of Pearson (Pearson and Lipman, 1988), by computerized implementations of these algorithms (GAP, BESTFIT, FASTA, and TFASTA in the Wisconsin Genetics Software Package Release 7.0, Genetics Computer Group, 575 Science Dr., Madison, Wis., or the Sequence Analysis Software Package of the Genetics Computer Group, University of Wisconsin, Madison, Wis.), or by inspection, and the best alignment (i.e., resulting in the highest percentage of homology over the comparison window) generated by the various methods is selected. The similarity of the two sequence (i.e., the probe sequence and the database sequence) can then be predicted.

Such software matches similar sequences by assigning degrees of homology to various deletions, substitutions and other modifications. The terms "homology" and "identity" in the context of two or more nucleic acids or polypeptide sequences, refer to two or more sequences or subsequences that are the same or have a specified percentage of amino acid residues or nucleotides that are the same when compared and aligned for maximum correspondence over a comparison window or designated region as measured using any number of sequence comparison algorithms or by manual alignment and visual inspection.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned.

One example of a useful algorithm is BLAST and BLAST 2.0 algorithms, which are described in Altschul et al., Nuc. Acids Res. 25:3389-3402 (1977) and Altschul et al., J. Mol. Biol. 215:403-410 (1990), respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0). The BLAST algorithm parameters W, T, and X determine the sensitivity and speed of the alignment. The BLASTN program (for nucleotide sequences) uses as defaults a word-length (W) of 11, an expectation (E) of 10, M=5, N=−4 and a comparison of both strands.

The BLAST algorithm also performs a statistical analysis of the similarity between two sequences (see, e.g., Karlin & Altschul, Proc. Natl. Acad. Sci. USA 90:5873 (1993)). One measure of similarity provided by BLAST algorithm is the smallest sum probability (P(N)), which provides an indication of the probability by which a match between two nucleotide sequences would occur by chance. For example, a nucleic acid is considered similar to a references sequence if the smallest sum probability in a comparison of the test nucleic acid to the reference nucleic acid is less than about 0.2, more preferably less than about 0.01, and most preferably less than about 0.001.

Sequence homology means that two polynucleotide sequences are homologous (i.e., on a nucleotide-by-nucleotide basis) over the window of comparison. A percentage of sequence identity or homology is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence homology. This substantial homology denotes a characteristic of a polynucleotide sequence, wherein the polynucleotide comprises a sequence having at least 60 percent sequence homology, typically at least 70 percent homology, often 80 to 90 percent sequence homology, and most commonly at least 99 percent sequence homology as compared to a reference sequence of a comparison window of at least 25-50 nucleotides, wherein the percentage of sequence homology is calculated by comparing the reference sequence to the polynucleotide sequence which may include deletions or additions which total 20 percent or less of the reference sequence over the window of comparison.

Sequences having sufficient homology can be further identified by any annotations contained in the database, including, for example, species and source information. Accordingly, in a typical sample, a plurality of nucleic acid sequences will be obtained, sequenced, contigs generated and corresponding homologous sequences from a database identified. This information provides a profile of the polynucleotides present in the sample, including one or more features associated with the polynucleotide including the organism and other source information associated with that sequence or any polypeptide encoded by that sequence based on the database information.

In some instances it may be desirable to RT-PCR portions of blank regions between contigs or fragments. Such methods can be used to fill in the blanks and improve fidelity of any homology searches. Methods of RT-PCR are known in the art.

In some instances it may be desirable to perform an amplification of the nucleic acid sequence present in a sample or a particular clone that has been isolated. In this embodiment, the nucleic acid sequence is amplified by PCR reaction or similar reaction known to those of skill in the art. Commercially available amplification kits are available to carry out such amplification reactions.

Furthermore, RACE, or Rapid Amplification of cDNA Ends, can be used to obtain the full length sequence of an RNA transcript found within a cell. RACE results in the production of a cDNA copy of the RNA sequence of interest, produced through reverse transcription, followed by PCR amplification of the cDNA copies. The amplified cDNA copies are then sequenced and, if long enough, should map to a unique mRNA already described, the full sequence of which is known. RACE can provide the sequence of an RNA transcript from a small known sequence within the transcript to the 5' end (5' RACE-PCR) or 3' end (3' RACE-PCR) of the RNA. The protocols for 5' or 3' RACES differ slightly. 5' RACE-PCR begins using mRNA as a template for a first round of cDNA synthesis (or reverse transcription) reaction using an anti-sense (reverse) oligonucleotide primer that recognizes a known sequence in the gene of interest; the primer is called a gene specific primer (GSP), and it copies the mRNA template in the 3' to the 5' direction to generate a specific single-stranded cDNA product. Following cDNA synthesis, the enzyme terminal deoxynucleotidyl transferase (TdT) is used to add a string of identical nucleotides, known as a homopolymeric tail, to the 3' end of the cDNA. A PCR reaction is then carried out, which uses a second anti-sense gene specific primer (GSP2) that binds to the known sequence, and a sense (forward) universal primer (UP) that binds the homopolymeric tail added to the 3' ends of the cDNAs to amplify a cDNA product from the 5' end. 3' RACE-PCR uses the natural polyA tail that exists at the 3' end of all eukaryotic mRNAs for priming during reverse transcription, so this method does not require the addition of nucleotides by TdT. cDNAs are generated using an Oligo-dT-adaptor primer that complements the polyA stretch and adds a special adaptor sequence to the 3' end of each cDNA. PCR is then used to amplify 3' cDNA from a known region using a sense GSP, and an anti-sense primer complementary to the adaptor sequence.

The following examples are intended to illustrate but not limit the disclosure. While they are typical of those that might be used, other procedures known to those skilled in the art may alternatively be used.

EXAMPLES

Example 1

Discovery of New Viruses

Discovery of new viruses from *Drosophila* cell line by VDsiR. The methods of the disclosure (VDsiR) were run on the small RNA library (GEO accession number: GSM361908 & GSM272652) constructed from the Schneider 2 cell line (S2) reported by Flynt et al (2009). Sequencing by the Illumina platform of this S2 cell line, came from the Gerald Rubin laboratory (S2-GMR) and was shown to be latently infected by FHV, yielded 6,922,433 small sequences in total, of which 1,254,333 were unique. A total of 1639 contigs were assembled by the Velvet program. Length of contigs range from 33 to 813 nt, and the mean and median size of contigs are 92 and 65 respectively. 1032 contigs can be mapped to the genome of D. melanogaster (>=90% coverage, >=90% similarity) and 635 of these contigs overlap with transposon loci. 51 contigs showed similarity to the bipartite (+)RNA genome of FHV supporting the conclusion of Flyn et al (2009). However, the analysis further showed that the persistent isolate of FHV in S2-GMR is identical to the TNCL isolate reported earlier in an S2 cell line (Li et al, 2007). The length of contigs of FHV virus vary from 33 bp to 339 bp with a mean size of 70 bp. 28 and 23 contigs were mapped to the genomic RNA1 and RNA2 of TNCL, respectively, covering 73% and 91% of the full-length RNAs.

All of the remaining contigs were compared first with the nucleotide sequences of known viruses in the NCBI databases. 46 contigs (33- to 401-nt in length) showed similarity with the bipartite dsRNA genome of *Drosophila* X virus (DXV). 75% of the DXV A segment (DXV-A) was covered by 21 contigs, whereas 99% of DXV-B was covered by 26 contigs.

Figure 2:
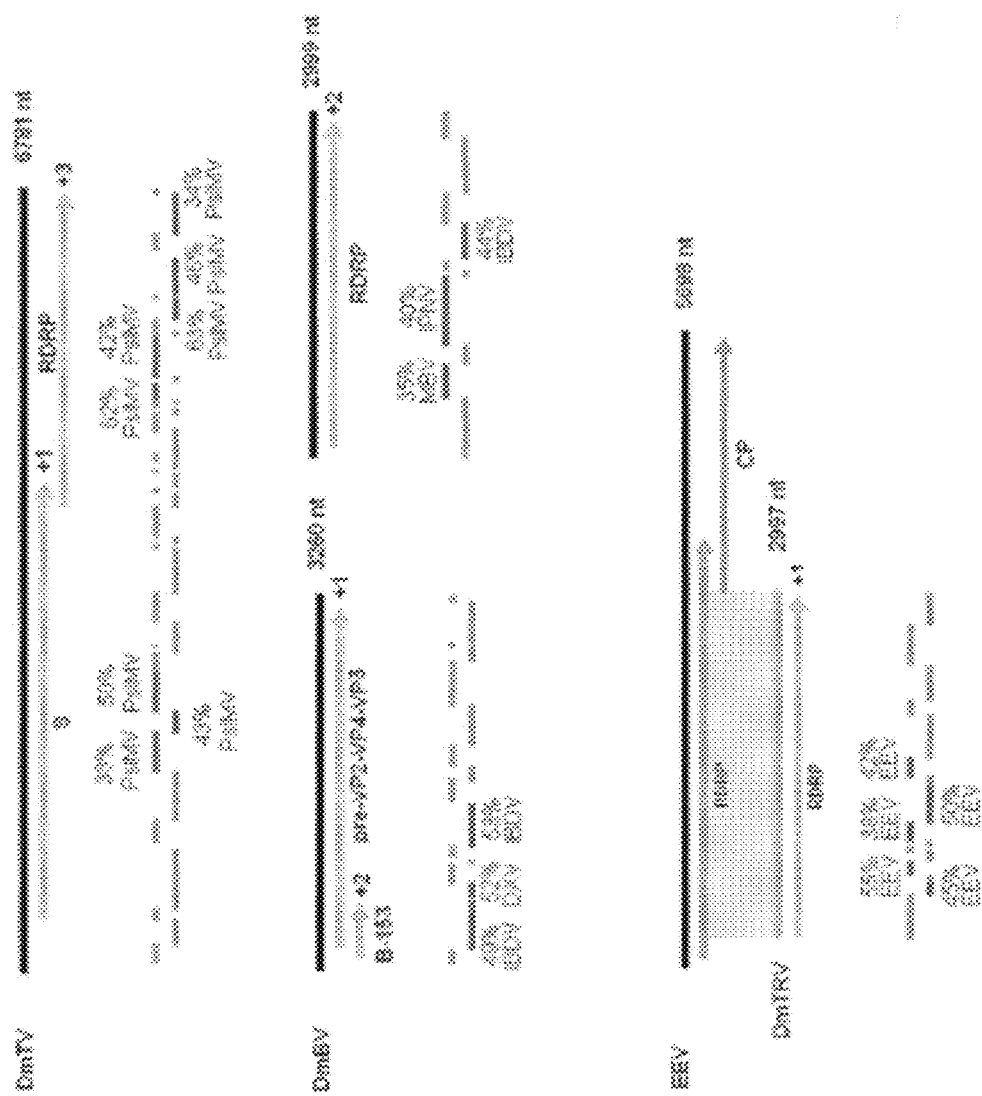
FIG. 2 shows the discovery of three new viruses by assembly of viral siRNAs. Total of 54, 34 and 19 contigs assembled from sequenced siRNAs were mapped to DmTV, DmBV and DmTRV, respectively. The genome organization of EEV was shown as a reference for DmTRV. % protein sequence identities of assembled contigs (red bars) of the three viruses to related viruses were shown on the top or below; as discussed in detail in Example 1, below.

In addition to contigs mapping to the *Drosophila* genome and to known virus (FHV and DXV), there are still 510 unassigned contigs. In silico translation of these contigs was further compared with proteins encoded by known viruses. 19 contigs (indicated as red bars in FIG. 2) show low similarity to and can be clustered within viral proteins encoded by members of virus families totiviridae, Birnaviridae, and tetraviridae, with the closest known virus being Penaeid shrimp infectious myonecrosis virus (PsIMV), infectious bursal disease virus (IBDV), and *Euprosterna elaeasa* virus (EEV), respectively (FIG. 2). PsIMV and IBDV are both dsRNA viruses whereas EEV is a positive-strand RNA virus. We tentatively named the dsRNA viruses as *Drosophila melanogaster* totivirus (DmTV) and *Drosophila melanogaster* birnavirus (DmBV), and the (+)-strand RNA virus as *Drosophila melanogaster* tetravirus (DmTRV).

Base on the orientation and relative positions of these contigs to the related viruses, primers were designed and the complete genome for the two dsRNA viruses were amplified by RT-PCR and 5'/3' RACE and completely sequenced. 31 and 20 additional unassigned contigs were mapped to the sequenced genomic RNAs of DmTV and DmBV, respectively (indicated as gray bars in FIG. 2). The sequenced siRNAs of DmTRV were assembled into a 3-kb contig, which encodes most of the viral RdRP. 403 contigs were unassigned so far. These unassigned contigs may correspond to novel viruses that show no detectable similarity to any of the known viruses although a number of them may map to the 3' half of the DmTRV genome yet to be obtained by RT-PCR.

Phylogenetic analyses of the viral RdRP sequences showed that all of the three identified viruses are new. These analyses, as illustrated in FIG. 3A, FIG. 3B and FIG. 3C, also suggested that DmTV and DmTRV might define two new virus genera and that DmTV forms a new genus with PsIMV, which was unassigned previously. Inoculation of un-contaminated S2 cells with the supernatant of GMR-S2 and subsequent Northern blot analyses showed that the three newly identified viruses are infectious. PsIMV, IBDV and Infectious pancreatic necrosis virus (IPNV) are all important pathogens in agriculture and fishery (Müller et al. 2003, Poulos et al. 2006). Thus, establishing a *Drosophila* model for related viruses would facilitate understanding pathogenesis.

Figure 3:
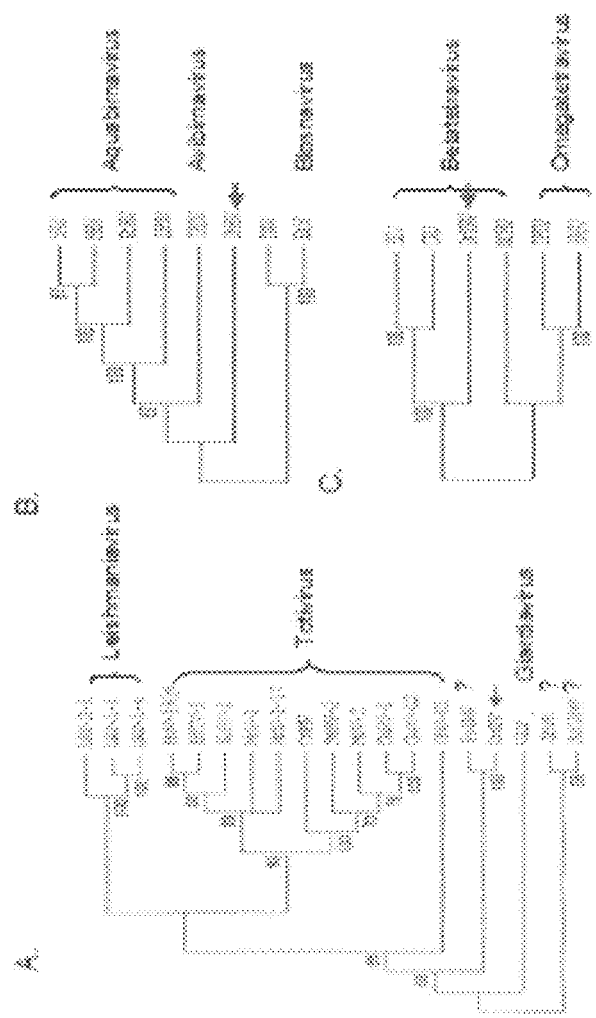
FIG. 3A, FIG. 3B, FIG. 3C illustrate a phylogenetic analysis of newly identified viruses (indicated by a red arrow) according to the similarities of viral RdRPs with Clustal W method; as discussed in detail in Example 1, below.

For FIG. 3, the phylogenetic trees were calculated by using the neighbor-joining method and the reliability of each branch was evaluated with bootstrap (1000 times repeat). The genera of each virus was listed on the right and "?" indicates a virus with an unassigned taxonomic status. The viruses used for phylogenetic analysis list below. *Leishmania* RNA virus 2-1 (LRV-2-1), *Leishmania* RNA virus 1-1 (LRV-1-1), *Leishmania* RNA virus 1-4 (LRV-1-4), *Helminthosporium victoriae* virus 190S (HvV-190S), *Botryotinia fuckeliana* totivirus 1 (BfTV-1), *Sphaeropsis sapinea* RNA virus 1 (SsRV-1), *Magnaporthe oryzae* virus 1 (MoV-1), *Helicobasidium mompa* No. 17 virus (HmV-1-17), *Coniothyrium minitans* mycovirus (CmMV), *Sphaeropsis sapinea* RNA virus 2 (SsRV-2), *Magnaporthe oryzae* virus 2 (MoV-2), *Gremmeniella abietina* RNA virus L1 (GaRV-1), *Gremmeniella abietina* RNA virus L1 (GaRV-2), *Ustilago maydis* virus H1 (UmV-H1), Penaeid shrimp infectious myonecrosis virus (PsIMV), *Giardia lamblia* virus (GLV), *Zygosaccharomyces bailii* virus Z (ZbVZ), Amasya cherry disease-associated mycovirus (AcDAMV), Yellowtail ascites virus (YAV), Marine birnavirus (MBV), *Paralichthys olivaceus* birnavirus (PoBV), Infectious pancreatic necrosis virus (IPNV), Infectious bursal disease virus (IBDV), *Drosophila* x virus (DXV), Blotched snakehead virus (BsV), *Euprosterna elaeasa* virus (EEV), hosea asigna virus (TAV), udaurelia capensis beta virus (NCBV), *Dendrolimus punctatus* tetravirus (DPTV), *Helicoverpa armigera* stunt virus (HASV).

Figure 4:
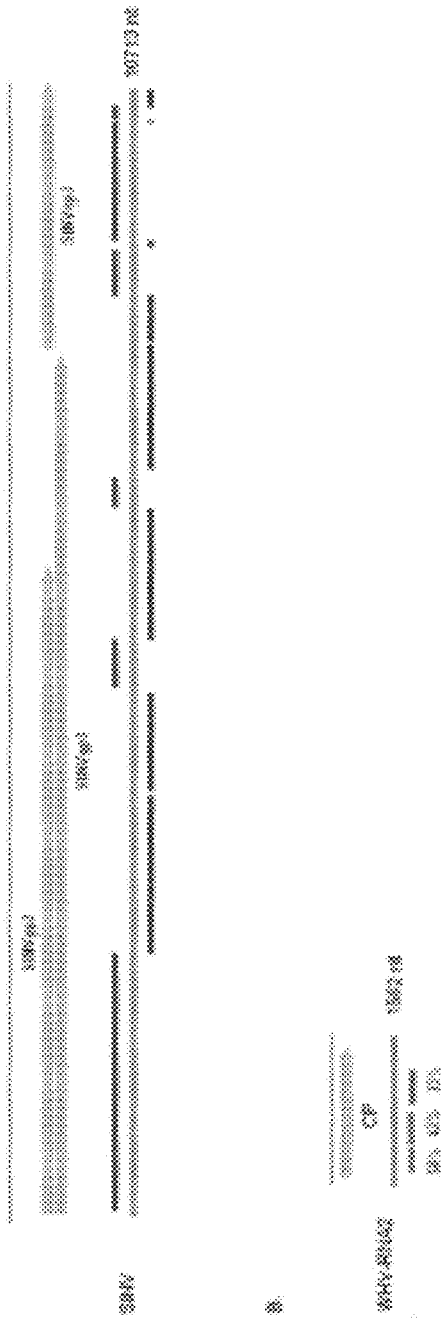
FIG. 4A and FIG. 4B illustrate the distribution of assembled viral siRNA contigs on the monopartite genome and bipartite RNA genome of SINV and a new nodavirus respectively; as discussed in detail in Example 1, below.

Discovery of a new virus from adult mosquitoes by VDsiR. The VDsiR system was also used to examine the reported small RNA library made from adult mosquitoes infected with SINV (Myles et al. 2008). As expected, contigs corresponding to SINV were readily assembled from the small RNA library (FIG. 4A). In addition, three contigs (covering 80% of the protein) show similarities with capsid precursor protein coding region of Wuhan nodavirus (FIG. 4B), which is an unassigned member of the Nodoviridae (Liu et al., 2006) (referred to herein as mosquito nodavirus A). These findings suggest that it is feasible to use the VDsiR system for virus discovery in mosquitoes. In FIG. 4, the genome of Wuhan Nodavirus (WHV) was shown as a reference for the new virus; and the percent (%) protein sequence identities of assembled contigs (red bars) of the new virus to WHV is shown.

Using the methods described herein, viral siRNAs produced by the host immune system are overlapping in sequence and can be assembled back into long fragments of the infecting viral RNA genome. Individual small RNAs of 21- to 24-nt in length derived from known viruses are readily identifiable by conventional programs (Aravin et al., 2003). However, these programs become less informative or do not work when viral siRNAs are derived from an infecting virus that differs significantly from any of the known viruses. We have recently sequenced the viral siRNAs produced by the *Drosophila* RNAi immune system in response to infection by a VSR-deficient mutant Flock house virus (FHV) (Aliyari et al., 2008). FHV contains a positive-strand RNA genome and encodes a VSR B2 protein that inhibits both the production and activity of viral siRNAs by binding to dsRNA and siRNA. Use of the 454 platform yielded 4371 small RNA sequences in total (18-28 nt), among which 1177 (27%) are FHV-specific. The major precursor of FHV siRNAs is the ~400-bp dsRNA corresponding to the 5'-terminal region of the FHV RNA genome so that most of the sequenced viral siRNAs are identical or complementary in sequence to this region of the genome. Unlike "phased" production of siRNAs from a defined end of synthetic dsRNA substrates and trans-acting siRNA precursors, however, Dicer-2 processing of the viral dsRNA in infected *Drosophila* cells initiate from multiple positions. As a result, the viral siRNAs produced are overlapping in sequence and can be assembled back into longer fragments of the FHV RNA genome (FIG. 1B) using computer programs for whole genome assembling from short reads (Warren et al. 2007, Jeck et al. 2007, Zerbino et al, 2008).

The methods were demonstrated with viral siRNAs using a small RNA library recently sequenced in the lab by the Illumina platform, which provides much more reads in a single run than the 454 platform. The library was constructed from small RNAs of *Arabidopsis thaliana* plants infected with cucumber mosaic virus (CMV), which contains a tripartite (+)-strand RNA genome. 2,036,929 sequences were collected of small RNAs that ranged 19-25 nt in length. These sequences were run through by the assembly program, and 114 contigs have been obtained. 46 contigs have identity with the CMV genome, 96% to approximately 99% regions of RNA1, RNA2 and RNA3 have been covered by these contigs. The largest contig come from RNA1 and is 2741 bp in length (FIG. 2A).

The following references are incorporated herein by reference.

Aliyari, R., and Ding, S. W. (2009). RNA-based viral immunity initiated by the Dicer family of host immune receptors. Immunol Rev 227, In press.

Aliyari R, Wu Q, Li H W, Wang X H, Li F, Green L D, Han C S, Li W X, Ding S W. Mechanism of induction and suppression of antiviral immunity directed by virus-derived small RNAs in *Drosophila*. Cell Host Microbe. 2008 Oct. 16; 4(4):387-97.

Delwart E L. Viral metagenomics. Rev Med Virol. 2007 March-April; 17(2):115-31.

Ding, S. W., and Voinnet, O. (2007). Antiviral immunity directed by small RNAs. Cell 130, 413-426.

Flynt A, Liu N, Martin R, Lai E C. Dicing of viral replication intermediates during silencing of latent *Drosophila* viruses. Proc. Natl. Acad. Sci. USA. 2009 Feb. 27. [Epub ahead of print]

Jeck, W. R., Reinhardt, J. A., Baltrus, D. A., Hickenbotham, M. T., Magrini, V., Mardis, E. R., Dangl, J. L., Jones, C. D. (2007) Extending assembly of short DNA sequences to handle error. Bioinformatics 23:2942-2944

Lang A S, Rise M L, Culley A I, Steward G F. RNA viruses in the sea. FEMS Microbiol Rev. 2009 March; 33(2):295-323.

Li H, Li W X, Ding S W. Induction and suppression of RNA silencing by an animal virus. Science. 2002 May 17; 296(5571):1319-21.

Li, W. X., Li, H., Lu, R., Li, F., Dus, M., Atkinson, P., Brydon, E. W., Johnson, K. L., Garcia-Sastre, A., Ball, L. A., et al. (2004). Interferon antagonist proteins of influenza and vaccinia viruses are suppressors of RNA silencing. Proc Natl Acad Sci USA 101, 1350-1355.

Li, F., and Ding, S. W. (2006). Virus counterdefense: diverse strategies for evading the RNA-silencing immunity. Annu. Rev. Microbiol 60, 503-531.

Li T C, Scotti P D, Miyamura T, Takeda N. Latent infection of a new alphanodavirus in an insect cell line. J Virol. 2007 October; 81(20):10890-6.

Myles K M, Wiley M R, Morazzani E M, Adelman Z N. Alphavirus-derived small RNAs modulate pathogenesis in disease vector mosquitoes. Proc Natl Acad Sci USA. 2008 Dec. 16; 105(50):19938-43. Epub 2008 Dec. 1.

Mlotshwa, S., Pruss, G. J., and Vance, V. (2008). Small RNAs in viral infection and host defense. Trends Plant Sci 13, 375-382.

Müller H, Islam M R, Raue R. Research on infectious bursal disease—the past, the present and the future. Vet Microbiol. 2003 Dec. 2; 97(1-2):153-65.

Poulos B T, Tang K F, Pantoja C R, Bonami J R, Lightner D V. Purification and characterization of infectious myonecrosis virus of penaeid shrimp. J Gen Virol. 2006 April; 87(Pt 4):987-96.

Sanchez-Vargas, I., Scott, J. C., Poole-Smith, B. K., Franz, A. W., Barbosa-Solomieu, V., Warren, R. L., Sutton, G. G., Jones, S. J. M., Holt, R. A. (2007) Assembling millions of short DNA sequences using SSAKE. Bioinformatics 4:500-501.

Wang X H, Aliyari R, Li W X, Li H W, Kim K, Carthew R, Atkinson P, Ding S W. RNA interference directs innate immunity against viruses in adult *Drosophila*. Science. 2006 Apr. 21; 312(5772):452-4.

Wilusz, J., Olson, K. E., and Blair, C. D. (2009). Dengue virus type 2 infections of *Aedes aegypti* are modulated by the mosquito's RNA interference pathway. PLoS Pathog 5, e1000299.

Zambon, R. A., Vakharia, V. N., and Wu, L. P. (2006). RNAi is an antiviral immune response against a dsRNA virus in *Drosophila melanogaster*. Cell Microbiol 8, 880-889.

Zerbino, D. R., Birney, E. (2008) Velvet: Algorithms for de novo short read assembly using de Bruijn graphs. Genome Res. 18:821-829.

Example 2

Discovery of New Viruses and Viral Genomes

In alternative embodiments the invention provides methods for viral genome assembly and viral discovery using small inhibitory RNAs, or "small silencing," RNAs (siRNAS), micro-RNAs (miRNAs) and/or PIWI-interacting RNAs (piRNAs), including siRNAS, miRNAs and/or piRNAs isolated or sequenced from invertebrate organisms such as insects (*Anthropoda*), nematodes (*Nemapoda*), *Mollusca, Porifera*, and other invertebrates, and/or plants, fungi or algae, *Cyanobacteria* and the like.

While the invention is not limited by any particular mechanism of action or natural process, the invention is based on plant and invertebrate response to infection. Invertebrates process replicating viral RNA genomes into small interfering RNAs (siRNAs) of discrete sizes to guide virus clearance by RNA interference. Here we show that viral siRNAs sequenced from fruitfly, mosquito and nematode cells were all overlapping in sequence, and the methods of the invention use these siRNAs for viral genome assembly and virus discovery.

To demonstrate how embodiments of the invention work, we examined contigs assembled from published small RNA libraries and discovered five new viruses from cultured *Drosophila* cells and adult mosquitoes, including three with a positive-strand RNA genome and two with a dsRNA genome. Notably, four of the identified viruses exhibited only low sequence similarities to known viruses so that none could be assigned into an existing virus genus. We also describe detection of the first virus-derived PIWI-interacting RNAs (piRNAs) in *Drosophila* and demonstrate viral genome assembly from viral piRNAs in absence of viral siRNAs.

Thus, this invention provides a powerful culture-independent approach for virus discovery in invertebrates by assembling viral genomes directly from host immune response products without prior virus enrichment or amplification. Viruses, including plant, fungal, algae and/or any invertebrate virus discovered by a method of this invention can include new human, plant and vertebrate viral pathogens that are transmitted by arthropod and plant vectors.

Results:

Virus genome sequencing by assembly of viral siRNAs produced in invertebrate hosts. The type III dsRNA-specific ribonuclease Dicer preferentially cleaves long dsRNA substrates from a terminus so that dsRNA precursors with a defined terminus are processed into siRNAs in 21-nucleotide (nt) phases (26-27). However, sequencing of small RNAs by the 454 platform from *Drosophila* cells acutely infected with FHV showed recently that the DCR2-dependent, 21-nt viral siRNAs are not produced in phase (11). Thus, we tested the idea that viral siRNAs produced by the host immune system might be overlapping in sequence by determining if the sequenced FHV siRNA fragments could be assembled back into the RNA genome of FHV.

We chose VELVET™ program (28) developed for genome assembly from short reads and set 17 nucleotides as the minimal overlapping length (k-mer: 17) required to join two small RNAs into a contig. Assembly of the sequenced 1177 FHV siRNAs (11) by VELVET™ yielded three contigs of 54, 73 and 52 nucleotides long, which contained 27, 47, 35 siRNAs, respectively (FIG. 5A). This indicated that viral siRNAs produced in infected fruit fly cells were indeed overlapping in sequence. All of the three assembled contigs were clustered in the 5'-terminal region of the genomic RNA1 of FHV (FIG. 5A), to which more than 60% of the RNA1-specific siRNAs were previously mapped (11).

Figure 5:
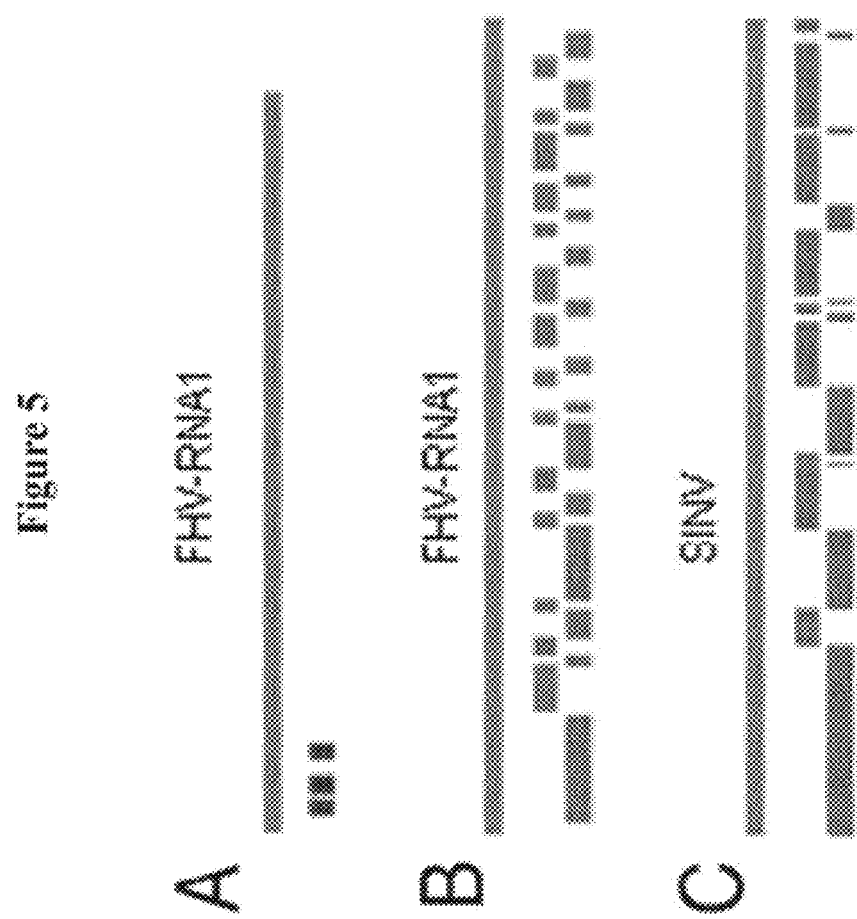
FIG. 5 illustrates position and distribution of FHV and SINV siRNA contigs assembled from small RNAs sequenced from (FIG. 5A) *Drosophila* S2 cells infected with the B2-deletion mutant of FHV (11), (FIG. 5B) a transgenic *C. elegans* strain in the RNAi-defective 1 (rde-1) mutant background carrying an FHV RNA1 replicon in which the coding sequence of B2 was replaced by that of GFP (29), and (FIG. 5C) adult mosquitoes infected with SINV (22); as discussed in detail in Example 2, below.

The nematode *Caenorhabditis elegans* carrying a self-replicating genomic RNA1 of FHV produces viral siRNAs detectable by Northern blot hybridization (29). A total of 1,236,800 small RNAs of 19-25 nucleotides were sequenced from the nematodes by the Illumina platform. In addition to 321,568 (26%) known *C. elegans* miRNAs, the library contained 5,957 (0.48%) and 1455 (0.12%) reads that were 100% identical/complementary to and differed by one nucleotide from the replicating FHV genome, respectively. The viral siRNAs were divided equally into (+) and (−) polarities and the most abundant viral siRNAs of both polarities were 23 nucleotides in length (FIG. 5), consistent with the size determined by Northern blot hybridization (29). Notably, assembly of the viral siRNAs cloned from *C. elegans* animals yielded 29 contigs that covered 93% of the FHV RNA1 by 36 times (FIG. 5B). There was also overlap with the neighboring contig for 21 of the 29 FHV contigs and lack of further assembly by Velvet was because the overlap length was shorter than the defined k-mer value (17-nt).

Cloning and sequencing of viral siRNAs produced in mosquitoes (*Aedes aegypti*) infected with the arthropod-borne Sindbis virus (SINV) were reported recently (22). The library contained 525,457 perfect-match SINV small RNAs and 68,669 SINV small RNAs with one mismatch. We found that assembly of the SINV small RNAs contained in the library generated 19 siRNA contigs with only 5 true gaps and that 99% of the 10-kb genome of SINV was covered by 1029 Times (see FIG. 5C).

These findings illustrate that high volume sequencing of total small RNAs from infected hosts yielded viral siRNA assemblies to cover almost the entire viral genomes by multiple times. Therefore, we conclude that viral siRNAs produced by the three invertebrate hosts are overlapping in sequence and could be used for viral genome assembly. Since production of viral siRNAs is an inevitable immune response of many eukaryotic hosts to virus infection (1-3), the methods of the invention can be used to discover new viruses by deep sequencing and assembly of total small RNAs accumulated in an organism of interest.

Discovery of four new RNA viruses from a *Drosophila* S2 cell line. To demonstrate that the vdSAR method of this invention worked, we analyzed two duplicate small RNA libraries constructed from a *Drosophila* Schneider 2 (S2) cell line previously maintained in Gerald Rubin's laboratory, termed as S2-GMR (12). These libraries contain 6,454,759 small RNAs of 18 to 28 nucleotides long in total, of which 1,092,833 molecules are unique. We first run the small RNA assembly program Velvet using k-mer of 17 and obtained 1639 contigs in total. BLASTN identified three groups of contigs that were identical or highly homologous to the nucleotide sequence entries of the non-redundant databases of NCBI. The first group of 1032 contigs was mapped to the genome of *D. melanogaster*, and 62% of those contigs overlapped transposon loci, suggesting that fruitfly endogenous siRNAs are also overlapping in sequence.

The second group of 49 contigs (33- to 401-nt in length) was found to correspond to the bipartite dsRNA genome of *Drosophila* X virus (DXV). 78% of the DXV genome segment A (23 contigs) and 91% of segment B (26 contigs) were obtained from the small RNA assemblies, yielding a total of 5.55 kb consensus RNA sequence with 73 times of coverage. Since the viral genome assembled from the sequenced small RNAs showed 98% identity to DXV (NC_004177, NC_004169) at both the nucleotide and protein sequence levels, we conclude that the S2-GMR cell line was persistently infected with DXV.

The third group included 57 contigs that exhibited strong homology to the bipartite +RNA genome of Tn5 cell line virus (TCLV). TCLV is a recently described member of the genus *Alphanodavirus* and shares 89.3% and 84% nucleotide sequence identity with RNA1 and RNA2 of FHV in the same genus (30). Assembly of siRNAs yielded 2,196 and 1,048 nucleotides in length for RNA1 and RNA2, respectively. The remaining parts of the bipartite genome were obtained by RT-PCR and RACE-PCR from S2-GMR cells provided by the Lai lab, producing the complete RNA1 and RNA2 molecules of 3107 and 1416 nucleotides long. The identified virus, designated American nodavirus (ANV), was most closely related to TCLV, with 94% and 92% identities to RNA1 and RNA2 of TCLV. ANV also shared 89% and 82% to RNA1 and RNA2 of FHV, which explained why it was thought previously that the cells were persistently infected by FHV (12). In addition to the RNA-dependent RNA polymerase (RdRP) and coat protein (CP), both TCLV and ANV encode the RNAi suppressor (protein B2) of 106 amino acid (aa) residues. However, the three viral proteins exhibited similar levels of sequence variations among ANV, TCLV and FHV, suggesting that ANV represents a new species of *Alphanodavirus*.

Three additional clusters of virus-specific contigs were identified among the remaining 501 assembled contigs by BLASTX comparison to the known viral proteins in NCBI (cut-off le-3). Eight contigs in the first cluster (FIG. 6A) encoded proteins with 34-62% identities to either the RdRP (5 contigs of 1410 nucleotides in length) or the structural protein (3 contigs of 899 nucleotides in length) of Penaeid shrimp infectious myonecrosis virus (PsIMNV) (31). PsIMNV is an unassigned member in the Totiviridae, which includes three established genera of viruses with a linear dsRNA genome (32). The complete genome of the identified virus, designated *Drosophila melanogaster* totivirus (DTV), was obtained from S2-GMR cells by RT-PCR using primers designed according to the sequences of the eight contigs and their relative positions mapped in the genome of PsIMNV (FIG. 6A), and by RACE-PCR. The genome of DTV was 6,780 nucleotides long and encoded CP and RdRP ORFs that overlapped by 205 nucleotides. Although the RdRPs of DTV and PsIMNV shared only 37.6% identities, phylogenetic analysis of the viral RdRPs in the Totiviridae showed that DTV and PsIMNV formed a distinct cluster outside of the known three genera (FIG. 6A). We thus suggest a new genus in the Totiviridae to include DTV and PsIMNV.

The second siRNA cluster also contained 8 contigs (FIG. 6B) encoding proteins with homology to various members of the Birnaviridae, which contains a bipartite dsRNA genome (33). Four of those contigs with a combined length of 1,224 nucleotides in total were mapped to the RdRP (VP 1) coding region whereas the remaining contigs of 888 nucleotides in length mapped to the second segment of the birnaviral genome that encodes for the structural proteins (FIG. 6B). The complete bipartite genome of the identified birnavirus, designated *Drosophila melanogaster* birnavirus (DBV), was recovered from S2-GMR cells by PCR as described above and cloned. Segment A of DBV was 3,258 nucleotides long, and encoded a polyprotein homologous to the known birnaviral structural proteins and an N-terminal overlapping protein, which however exhibited no similarities to the N-terminal overlapping proteins encoded by several birnaviruses (33). Segment B was 3,014 nucleotides long and encoded the viral RdRP (FIG. 6B). Sequence and phylogenetic analyses indicate that DBV is clearly distinct from all of the known birnaviruses including DXV, the only reported birnavirus isolated from an insect host (33). For example, neither of the predicted RdRP and structural proteins of DBV shares higher than 31% identities with any member of the three known birnaviral genera (FIG. 6B). Thus, we suggest that DBV represents a new species and genus in the Birnaviridae.

The last siRNA cluster contained two contigs (FIG. 6C) encoding proteins homologous to RdRP of *Euprosterna elaeasa* virus (EEV) from the Tetraviridae, members of which contain a +RNA genome. The combined length of the two contigs was 892 nucleotides. Repeated attempts to recover the viral genome from the S2-GMR cell line established in UC-Riverside by RT-PCR were unsuccessful. However, inclusion of an additional small RNA library (NCBI-GEO: GSM 272653) constructed from *Drosophila* Kc cell line by the Lai lab (12) in the assembly yielded a long contiguous contig of 3,005 nucleotides in length. This long contig contained the two initially identified contigs and 17 additional contigs in the S2-GMR libraries that did not exhibit detectable homology to known viral proteins (red and grey bars in FIG. 6C). The assembled siRNA consensus sequence encoded a protein of 984 residues, which shared approximately 29% identities with the RdRP of both EEV and *Thosea asigna* virus (TAV) in the Tetraviridae. Further phylogenetic analysis of the RdRPs in the Tetraviridae (FIG. 6C) suggests that the identified virus, designated *Drosophila melanogaster* tetravirus (DTrV), represents a new species in the Tetraviridae.

These results indicate that the S2-GMR cells used for library construction were persistently infected with five RNA viruses, belonging to four different virus families. As expected, we showed that the S2-GMR cell line established subsequently at UC-Riverside indeed contained infectious DXV, ANV, DTV and DBV, but not DTrV, by inoculation of healthy S2 cells followed by RT-PCR analysis (see FIG. 7A). These results explained that whereas we were successful in obtaining the full-length genome sequences of ANV, DTV and DBV, our repeated attempts to recover DTrV failed. 388,289 (6%) of the total 6,454,759 reads from the S2-GMR cells and 220 of the 1639 assembled contigs were mapped to the five viruses. The most predominant species of small RNAs derived from either the three dsRNA viruses (DTV, DBV and DXV) or the two +RNA viruses (ANV and DTrV) was 21-nucleotide (FIG. 7B), and the ratios of (+) and (−) 21-nt viral siRNAs were approximately equal (FIG. 7B). These features of virus-derived small RNAs were similar to those of FHV-derived siRNAs produced by DCR-2 (11), suggesting a shared biogenesis pathway for viral siRNAs targeting +RNA and dsRNA viruses in *D. melanogaster*.

There were major differences in the relative abundance of siRNAs derived from each of the five viruses, with 56%, 18.1%, 17.1%, 5.7%, and 3.4% of the total viral siRNA assigned to ANV, DTV, DBV, DXV, and DTrV, respectively. Further analysis indicated that the highest siRNA density targeting ANV was most likely due to the presence of a 591-nt defective-interfering RNA (DI-RNA) derived from ANV. We cloned the DI-RNA and found that 51% of the total viral siRNAs of the S2-GMR cells were mapped to the three siRNA peaks of ANV RNA2, which corresponded precisely to the regions of RNA2 (nucleotide 1-245, 515-712, 1250-1277 and 1297-1416) present in the DI-RNA (FIG. 7B and FIG. 7C). Northern blot hybridization (FIG. 7B) revealed that the DI-RNA replicated to high levels in S2-GMR cells (right lane), but to a much lower level in fresh healthy S2 cells inoculated with the supernatant of the S2-GMR cells (left lane), indicating that high replication levels of DI-RNA may be a key feature of the mix viral infection in the S2-GMR cells. In addition to the DI-RNA-derived siRNA peaks in ANV RNA2, the distribution of viral siRNAs was also not uniform along the remaining viral genomic RNAs (FIG. 4), as noted previously (16-20). However, our analyses indicated that the high siRNA density regions of the viral RNA genomes were associated with neither unusual AU content (53%) nor strong secondary structures.

Assembly of siRNAs and virus discovery in mosquitoes and *C. elegans*. We next demonstrated that the vdSAR method of this invention also worked in other invertebrates. The mosquito small RNA library reported by Myles and colleagues contained 3,771,297 reads of 18-26 nucleotides in length, representing 756,219 unique sequences (22). Except for the 19 contigs mapped to the Sinbis viral genome, no additional virus-specific contigs were identified by BLASTN. However, BLASTX searches of the remaining 435 contigs of small RNAs identified two contigs (FIG. 6D), which encoded proteins exhibiting 54% and 72% similarities to the CP precursor of Wuhan nodavirus (WNV). WNV, an insect virus identified recently, is an unassigned member of the Nodaviridae (34-35). The combined length of the two contigs was 1103 nucleotides and the encoded protein covered 83% of, and shared 41.6% identity with, the WNV CP precursor. Thus, the identified virus may represent a new virus, designated as Mosquito nodavirus (MNV). Phylogenetic analysis of the nodaviral CPs indicates that MNV does not belong to either of the established genera in the Nodaviridae (FIG. 6D).

The total small RNAs we sequenced from *C. elegans* strain N2 were assembled into 117 contigs in total. However, except for the 29 FHV-specific contigs, no additional virus-specific contigs were identified by either BLASTN or BLASTX. Similarly, none of the 172 contigs assembled from a large library of 10,964,021 small RNAs constructed from mix stages of C. elegans (36) exhibited detectable similarities to known viruses. This suggests that the common lab strain of C. elegans might not be persistently infected with an RNA virus of sufficient homology detectable by vdSAR.

Detection and assembly of virus-derived piRNAs in Drosophila ovary somatic sheet cells. We further carried out assembly of the small RNAs sequenced recently from a Drosophila ovary somatic sheet (OSS) cell line (37). Unlike S2 cells isolated originally from late embryonic stages that do not express any of the three PIWI subfamily members, OSS cells produce abundant primary piRNAs of 24-30 nucleotides in addition to siRNAs and miRNAs due to the expression of the PIWI protein (37-39). BLASTN searches of the assembled contigs readily identified six RNA viruses in the OSS cells. These include DXV, ANV, DBV and DTrV, all of which were also detected in S2-GMR cells, as well as Drosophila C virus (DCV) and Nora virus. DCV and Nora virus belong to different +RNA virus families and both share similarities with picornaviruses. A common source of virus contamination for the two cell lines might be extracts from infected flies used in cell culture (37). BLASTX searches of the remaining assembled contigs did not identify additional viruses. 3.3% of the total 36,389,371 reads from the OSS cells were mapped to the six viruses. Among the 1,184,811 viral siRNAs in total, 31.4%, 26.9%, 17%, 13.5%, 7.1% and 4% came from DCV, Nora, DXV, DBV, FHV and DTrV respectively. Thus, ANV was not the predominant target for dicing in the OSS cells and consistently, mapping of the siRNAs to individual genomic RNAs did not identify the three siRNA peaks corresponding to the regions specific to the DI-RNA of RNA2 detected in the S2-GMR cells.

Notably, we found a new population of virus-derived small RNAs in the OSS cells (FIG. 8A) that was not detected in S2-GMR cells. We suggest that they represent virus-derived piRNAs because of the following three shared features with the endogenous primary piRNAs detected in OSS cells (37-39). First, these viral piRNAs were 24 to 30 nucleotides in length with two peaks at 27 and 28 nucleotides (FIG. 8A). Second, viral piRNAs exhibited strong 5' uridine bias (approximately 63%) but no preference for adenine at the tenth position (FIG. 8B) and thus were distinct from Drosophila ovary secondary piRNAs loaded in AGO3, 73% of which have adenine at the 10th position (38). Third, viral piRNAs were almost exclusively (95%) one polarity (FIG. 8A). By comparison, viral siRNAs were shorter than viral piRNAs and exhibited no strand bias or preference for a particular nucleotide at any position. In addition, the relative abundance of viral piRNAs was highly variable among the six RNA viruses persistently infecting the OSS cells. Viral piRNAs targeting ANV and DCV were much more abundant than those targeting the remaining four viruses. Strikingly, ANV-specific piRNAs were more than twice as abundant as viral siRNAs in the OSS cells. Nevertheless, piRNAs of all six viruses were highly biased for sense reads, corresponding to either the genomic RNA of +RNA viruses (ANV, DCV, DTrV and Nora virus) or the mRNA-sense strand of the dsRNA viruses (DXV and DBV), and these viral pRNAs exhibited 5' U bias in only sense but not antisense reads (FIG. 8B).

Figure 8:
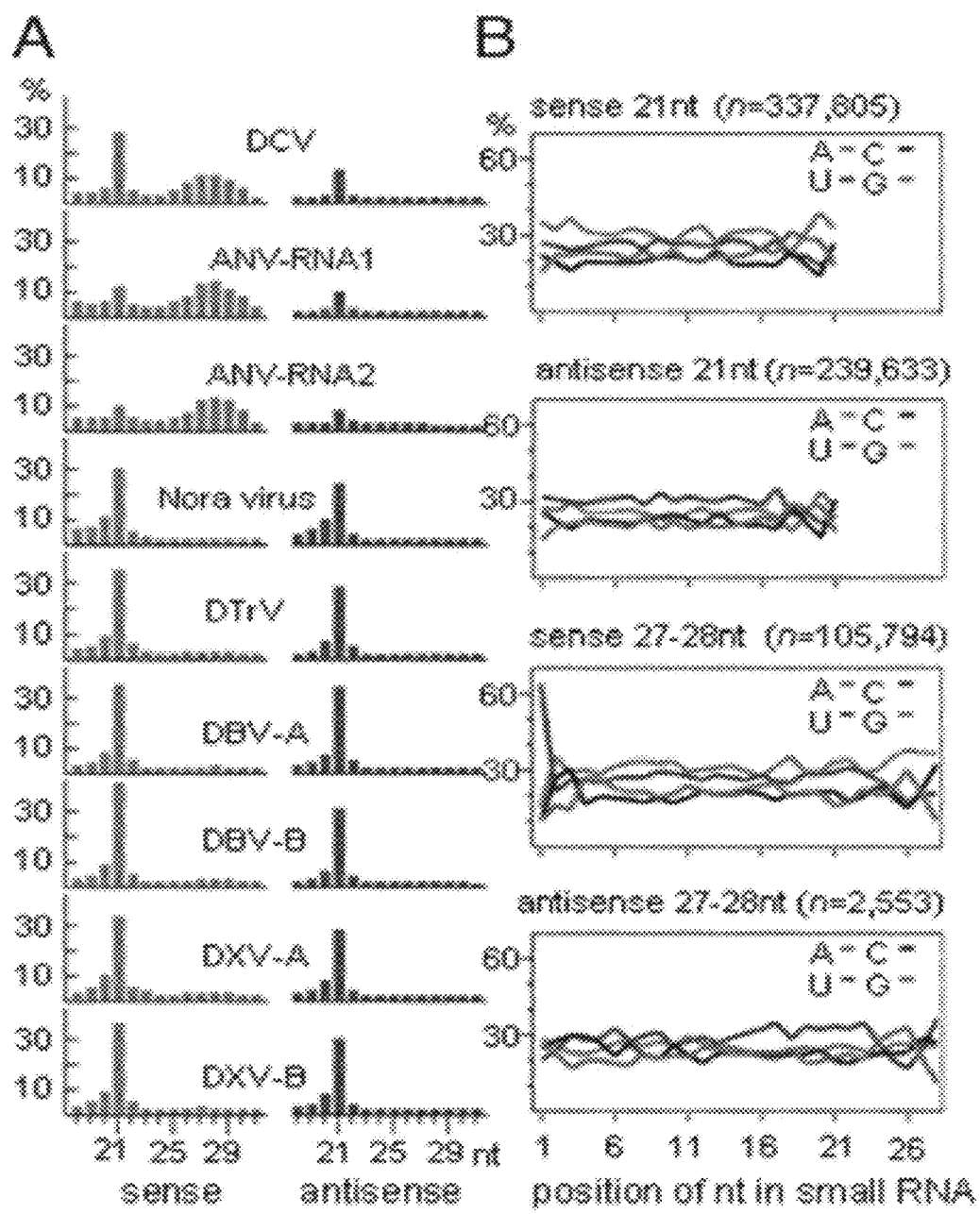
FIG. 8 illustrates size distribution (FIG. 8A) and aggregate nucleotide composition (FIG. 8B) of virus-derived small RNAs in *Drosophila* OSS cells; as discussed in detail in Example 2, below.

We next determined if these six viruses could be identified by assembly of viral piRNAs in the absence of viral siRNAs. To this end, 19,334,507 reads (3,298,838 unique sequences) from 25 to 30 nucleotides were sorted out of the OSS cell libraries. We found that all of the six viruses were identified by assembly of these siRNA-free piRNA reads followed by BLASTN, regardless of their relative piRNA abundance. 28 contigs were mapped to ANV, covering 94% and 99% of RNA1 and RNA2, respectively. 92% of the DCV genome was represented by 68 assembled contigs. For the remaining four viruses that yielded less piRNAs, a total of 205 virus-specific piRNA contigs were identified, covering 83% to 95% of either the complete genomes of DBV, DXV and Nora virus or the partial DTrV genome (FIG. 8). However, BLASTX searches of the remaining assembled contigs did not identify additional viruses including DTV, consistent with the results from the assembly of viral siRNAs.

Discussion

In this study, we describe an embodiment of this invention, a vdSAR approach for virus discovery in invertebrates (and plant, algae and the like) by deep sequencing and assembly of viral small silencing RNAs produced by host immune machinery in response to infection. vdSAR was based on the observation that viral small silencing RNAs produced by fruitfly, mosquito and nematode cells were all overlapping in sequence. In this embodiment, total small RNAs were isolated from a host, sequenced in a single Illumina lane, and assembled into contigs by Velvet. Virus-specific contigs were identified by searching the non-redundant nucleotide sequence entries of NCBI both before (BLASTN) and after in silico translation (BLASTX), and the complete genomes of the viruses identified could subsequently be recovered by PCR and cloned. Use of vdSAR revealed persistent mix infection of Drosophila S2-GMR and OSS cell lines by five and six RNA viruses, respectively. Viral siRNA contigs were also assembled and identified from acutely infected Drosophila S2 cells and adult mosquitoes (FIG. 5A and FIG. 5C). However, no virus was identified by vdSAR from the N2 laboratory strain of C. elegans. Thus, it may be necessary to examine field isolates (40) for virus discovery in C. elegans since laboratory maintenance of worm strains often involves multiple rounds of bleaching to start worm cultures from eggs by removing larvae and adult animals and associated microbial contamination.

Five of the viruses assembled from fly and mosquito small RNAs were new and include three +RNA viruses and two dsRNA viruses. Except for ANV, DBV, DTV, DTrV and MNV all exhibited low sequence identities (25-42%) to known viruses that were detectable only in short regions of the encoded viral proteins. As a result, none of the four viruses could be assigned into an existing virus genus. This suggests that vdSAR is capable of discovering new viruses that are only distantly related to known viruses. It should be pointed out that viruses discovered by vdSAR from invertebrates may include those human and vertebrate viral pathogens that are transmitted by arthropod vectors. The identification of two new DNA viruses has been reported in sweet potato plants by an approach similar to vdSAR (see reference 41), indicating that vdSAR works in both plants and invertebrates.

Analysis of the recently reported small RNA libraries made in Drosophila OSS cells identified virus-derived piRNAs. This finding suggests for the first time that piRNAs may have an antiviral role, in addition to their role in genome defense against transposons (4-6). However, it is interesting to note that these viral piRNAs are also overlapping in sequence and can be used for viral genome assembly in absence of viral siRNAs. This suggests that vdSAR is likely to be effective for hosts or host tissues that may produce viral piRNAs only.

Discovery of new animal viruses is often hindered by difficulties in their amplification in cell culture and/or lack of their cross-reactivity in serological and nucleic acid hybridization assays to known viruses. Many new viruses have been recently identified in environmental and clinical samples using metagenomic approaches, in which viral particles are first partially purified and viral nucleic acid sequences randomly amplified prior to subcloning and sequencing (42-44). Both the metagenomic approaches and vdSAR are culture-independent and can identify viruses that share only low sequence similarities with the known viruses. By comparison, the methods of this invention require neither viral particle purification nor viral nucleic acid sequence amplification. Moreover, in some embodiments methods of this invention involve sequencing of the fraction of host small RNAs and data mining of only those small RNAs that can assemble into contigs so that both the amount of sequencing and data complexity are greatly reduced. Embodiments of methods of this invention can assemble viral genomes from the products of an active host immune response to infection. In some embodiments, only the replicating and infectious viruses that induce the immune response are identifiable by vdSAR.

Given the genetic and structural diversity of the characterized viruses, it is possible that there are novel types of viral and subviral pathogens that exhibit no similarity to any of the known viruses detectable by the available bioinformatic tools. These novel viruses would readily escape detection by the current homology-dependent metagenomic approaches and vdSAR. Indeed, a number of the assembled contigs from the *Drosophila* cells exhibit no detectable similarity to entries in NCBI databases. In this regard, the unique features of vdSAR may facilitate development of new bioinformatic tools for selecting particular contigs for virus discovery. For example, small RNA densities, small RNA size distribution patterns, and positive/negative strand ratios of small RNAs in the assembled contigs that are consistent with viral small silencing RNAs may all be considered as indicators of contigs with a viral origin.

Materials and Methods

Cell culture. Culture, virus infection of S2 cells and Northern blot hybridization were as described (11). The S2-GMR cell line was kindly provided by Eric Lai. The supernatant of S2-GMR cells established at UC-Riverside were used for infection of fresh healthy S2 cells.

Sequencing, assembly and analysis of small RNA libraries. The small RNA library of *C. elegans* was constructed as described (45) and sequenced by Illumina 2G ANA-LYZER™ at the campus Genomics Institute core facility for Genomics. Other small RNA libraries were retrieved from GEO database. The genome sequence of *D. melanogaster* and repeat annotation file were downloaded from UCSC (http://genome.ucsc.edu/). The nr and nt databases were downloaded from NCBI (updated on January, 2009). Velvet was downloaded from EBI (http://www.ebi.ac.uk/~zerbino/velvet). Mapping of small RNAs and assembled contigs to fly and viral genomes were done by BLASTN program using the standard parameters in genome assembly (contigs or viral contig is >=90% similarity and >=90% coverage of contigs). Assembled contigs were also examined for similarity of their encoded proteins to databases using BLASTX program. Additional data analyses were carried out with in-house Perl scripts. The computation analyses were carried out using the campus Genomics Institute core facility for Bioinformatics.

RT-PCR, RACE-PCR and sequencing. Reverse transcription (RT) and PCR were used to fill the gaps between siRNA contigs using primers designed according to the consensus sequences of the specific contigs involved and their relative positions mapped in the closely related viral genome. RT-PCR products were sequenced directly by conventional ABI dideoxyl sequencing. 5' RACE was carried out following the instruction of manufacturer (Invitrogen). For 3'-RACE, the total RNA was isolated from fly cells by the Trizol protocol, denatured at 65° C. for 5 min, and ligated to a preadynated 3' adaptor ppACACTCGGGCACCAAGGA (SEQ ID NO:1) (linker2, IDT Company, USA) with T4 RNA ligase truncated fragment (New England Biolabs, USA) (46). Following ethanol precipitation, the ligation products were reverse transcribed by SUPERSCRIPT III™ (Invitrogen, Carlsbad, Calif.), amplified by PCR. 5-RACE and 3' RACE product were cloned in pGEM-T easy vector (Promega, USA) before ABI dideoxyl sequencing. The Phred-Phrap-consed package was used for virus genome assembly.

Phylogenetic analysis. Mega 4 package was used to build the phylogenetic trees. Alignment of proteins was performed with Clustal W method, and the phylogenetic tree was calculated by using the neighbor-joining method. The reliability of each branch was evaluated with bootstrap (1000 times repeat).

Figure Legends for Example 2

FIG. 5 illustrates position and distribution of FHV and SINV siRNA contigs assembled from small RNAs sequenced from (FIG. 5A) *Drosophila* S2 cells infected with the B2-deletion mutant of FHV (11), (FIG. 5B) a transgenic *C. elegans* strain in the RNAi-defective 1 (rde-1) mutant background carrying an FHV RNA1 replicon in which the coding sequence of B2 was replaced by that of GFP (29), and (FIG. 5C) adult mosquitoes infected with SINV (22). Note that the length of RNA genomes was not drawn to scale.

Figure 6:
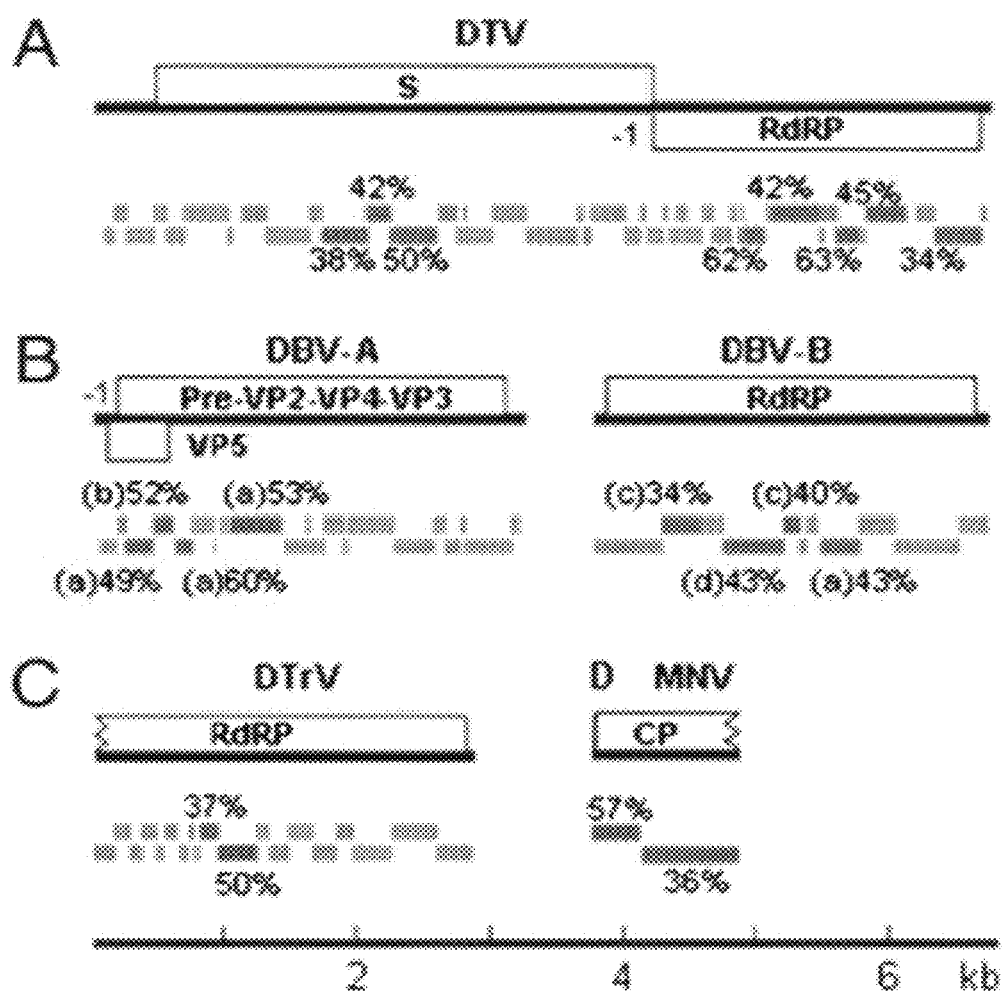
FIG. 6 illustrates discovery of dsRNA viruses DTV (FIG. 6A) and DBV (FIG. 6B), and +RNA viruses DTrV (FIG. 6C) and MNV (FIG. 6D) from S2-GMR cells by vsSAR; as discussed in detail in Example 2, below.

FIG. 6 illustrates discovery of dsRNA viruses DTV (FIG. 6A) and DBV (FIG. 6B), and +RNA viruses DTrV (FIG. 6C) and MNV (FIG. 6D) from S2-GMR cells by vsSAR. Red bars refer to the virus-specific contigs initially identified by % sequence similarities of their encoded proteins to a viral protein in the databases. The contigs of DTV, DTrV and MNV showed the highest similarities to PsIMV, EEV and WNV, respectively. However, four different members in the Birnaviridae were identified as the closest to DBV contigs: a—Infectious bursal disease virus (IBDV); b—DXV; c—Marine birnavirus (MAV); d—Blotched snakehead virus (BSV). Grey bars refer to the contigs that were assembled from small RNAs of S2-GMR cells and subsequently mapped to specific viruses after the complete genomes were obtained. Note that the length of RNA genomes was drawn to scale and the open reading frames encoded by the partial genome of DTrV (3005 nt) and MNV (1130 nt) were incomplete.

Figure 7:
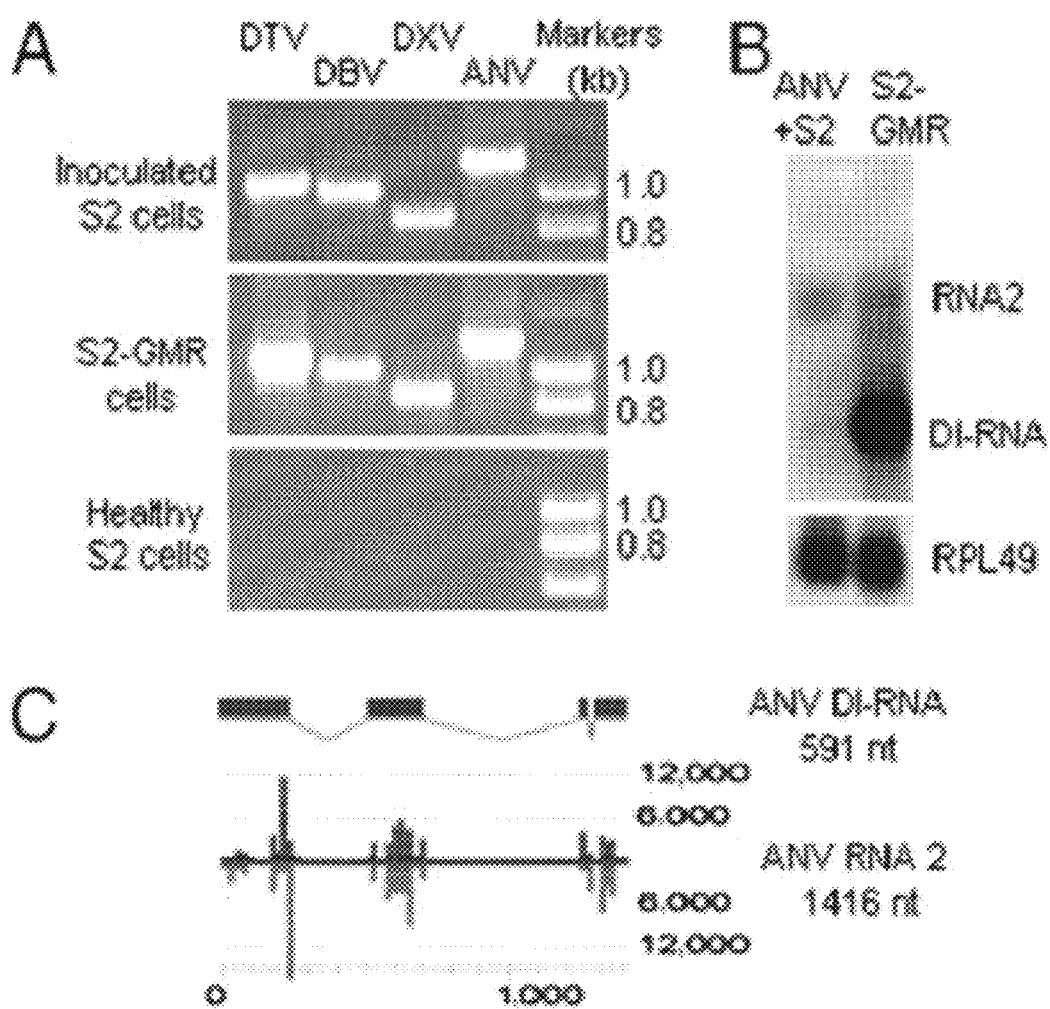
FIG. 7 illustrates the S2-GMR cells contained four infectious RNA viruses.

FIG. 7 illustrates the S2-GMR cells contained four infectious RNA viruses. FIG. 7A illustrates that DTV, DBV, DXV and ANV were all detected by RT-PCR in non-contaminated S2 cells 4 days after inoculation with the supernatant of the S2-GMR cells. Healthy S2 cells and the S2-GMR cells were used as controls. Primers used for RT-PCR were expected to yield specific products of 1,087, 1,030, 865 and 1,212 bp in length from DTV, DBV, DXV and ANV, respectively. FIG. 7B illustrates detection of a DI-RNA derived from ANV RNA2 in S2-GMR cells (right lane) and in S2 after inoculation with the supernatant of S2-GMR cells (left lane) by Northern blot hybridizations using a probe recognizing the 3'-terminal 120 nt of RNA2. FIG. 7C illustrates structure of the cloned DI-RNA of ANV (top) and mapping of the perfect-matched 21-nt siRNAs sequenced from S2-GMR cells to the positive (blue) and negative (red) strands of ANV RNA2 (20-nt windows) (bottom).

FIG. 8 illustrates size distribution (FIG. 8A) and aggregate nucleotide composition (FIG. 8B) of virus-derived small RNAs in *Drosophila* OSS cells. For each viral genome or genome segment, % of either sense (red bar) or antisense (blue bar) viral small RNAs of distinct sizes over total reads in length of 18-31 nt with perfect match was shown in FIG. 8A. % aggregate nucleotide compositions for all viral reads of 21-nt siRNA or 27 nt+28-nt piRNAs were calculated with the total numbers of reads in each size shown in parentheses.

REFERENCES

Example 2

1. Aliyari R & Ding S W (2009) RNA-based viral immunity initiated by the Dicer family of host immune receptors. *Immunol Rev* 227:176-188.
2. Mlotshwa S, Pruss G J, & Vance V (2008) Small RNAs in viral infection and host defense. *Trends Plant Sci* 13(7):375-382.
3. Ding S W & Voinnet O (2007) Antiviral immunity directed by small RNAs. *Cell* 130(3):413-426.
4. Ghildiyal M & Zamore P D (2009) Small silencing RNAs: an expanding universe. *Nat Rev Genet* 10(2):94-108.
5. Siomi M C, Saito K, & Siomi H (2008) How selfish retrotransposons are silenced in *Drosophila* germline and somatic cells. *FEBS Lett* 582(17):2473-2478.
6. Malone C D & Hannon G J (2009) Small RNAs as guardians of the genome. *Cell* 136(4):656-668.
7. Galiana-Arnoux D, Dostert C, Schneemann A, Hoffmann J A, & Imler J L (2006) Essential function in vivo for Dicer-2 in host defense against RNA viruses in *drosophila*. *Nat Immunol* 7(6):590-597.
8. Wang X H, et al. (2006) RNA interference directs innate immunity against viruses in adult *Drosophila*. *Science* 312(5772):452-454.
9. van Rij R P, et al. (2006) The RNA silencing endonuclease Argonaute 2 mediates specific antiviral immunity in *Drosophila melanogaster*. *Genes Dev* 20(21):2985-2995.
10. Li H W, Li W X, & Ding S W (2002) Induction and suppression of RNA silencing by an animal virus. *Science* 296(5571):1319-1321.
11. Aliyari R, et al. (2008) Mechanism of induction and suppression of antiviral immunity directed by virus-derived small RNAs in *Drosophila*. *Cell Host Microbe* 4(4):387-397.
12. Flynt A, Liu N, Martin R, & Lai E C (2009) Dicing of viral replication intermediates during silencing of latent *Drosophila* viruses. *Proc Natl Acad Sci USA*. 106:5270-5
13. Zambon R A, Vakharia V N, & Wu L P (2006) RNAi is an antiviral immune response against a dsRNA virus in *Drosophila melanogaster*. *Cell Microbiol* 8(5):880-889.
14. Hamilton A J & Baulcombe D C (1999) A species of small antisense RNA in posttranscriptional gene silencing in plants. *Science* 286(5441):950-952.
15. Vaucheret H (2008) Plant ARGONAUTES. *Trends Plant Sci* 13(7):350-358.
16. Molnar A, et al. (2005) Plant virus-derived small interfering RNAs originate predominantly from highly structured single-stranded viral RNAs. *J Virol* 79(12):7812-7818.
17. Ho T, Pallett D, Rusholme R, Dalmay T, & Wang H (2006) A simplified method for cloning of short interfering RNAs from *Brassica juncea* infected with Turnip mosaic potyvirus and Turnip crinkle carmovirus. *J Virol Methods* 136(1-2):217-223.
18. Qi X, Bao F S, & Xie Z (2009) Small RNA deep sequencing reveals role for *Arabidopsis thaliana* RNA-dependent RNA polymerases in viral siRNA biogenesis. *PLoS ONE* 4(3):e4971.
19. Donaire L, et al. (2009) Deep-sequencing of plant viral small RNAs reveals effective and widespread targeting of viral genomes. *Virology* 392(2):203-214.
20. Wang X B, et al. (2009) RNAi-mediated viral immunity requires amplification of virus-derived siRNAs in *Arabidopsis thaliana*. *Proc Natl Acad Sci USA*. In press.
21. Brackney D E, Beane J E, & Ebel G D (2009) RNAi targeting of West Nile virus in mosquito midguts promotes virus diversification. *PLoS Pathog* 5(7):e1000502.
22. Myles K M, Wiley M R, Morazzani E M, & Adelman Z N (2008) Alphavirus-derived small RNAs modulate pathogenesis in disease vector mosquitoes. *Proc Natl Acad Sci USA* 105(50):19938-19943.
23. Sanchez-Vargas I, et al. (2009) Dengue virus type 2 infections of *Aedes aegypti* are modulated by the mosquito's RNA interference pathway. *PLoS Pathog* 5(2): e1000299.
24. Segers G C, Zhang X, Deng F, Sun Q, & Nuss D L (2007) Evidence that RNA silencing functions as an antiviral defense mechanism in fungi. *Proc Natl Acad Sci USA* 104(31):12902-12906.
25. Zhang X, Segers G C, Sun Q, Deng F, & Nuss D L (2008) Characterization of hypovirus-derived small RNAs generated in the chestnut blight fungus by an inducible DCL-2-dependent pathway. *J Virol* 82(6):2613-2619.
26. Zhang H, Kolb F A, Brondani V, Billy E, & Filipowicz W (2002) Human Dicer preferentially cleaves dsRNAs at their termini without a requirement for ATP. *EMBO J.* 21(21):5875-5885.
27. Vagin V V, et al. (2006) A distinct small RNA pathway silences selfish genetic elements in the germline. *Science* 313(5785):320-324.
28. Zerbino D R & Birney E (2008) Velvet: algorithms for de novo short read assembly using de Bruijn graphs. *Genome Res* 18(5):821-829.
29. Lu R, Yigit E, Li W X, & Ding S W (2009) An RIG-I-Like RNA helicase mediates antiviral RNAi downstream of viral siRNA biogenesis in *Caenorhabditis elegans*. *PLoS Pathog* 5(2):e1000286.
30. Li T C, Scotti P D, Miyamura T, & Takeda N (2007) Latent infection of a new alphanodavirus in an insect cell line. *J Virol* 81(20):10890-10896.
31. Poulos B T, Tang K F, Pantoja C R, Bonami J R, & Lightner D V (2006) Purification and characterization of infectious myonecrosis virus of penaeid shrimp. *J Gen Virol* 87(Pt 4):987-996.
32. Hanizlik T N, et al. (2005) Totiviridae. *Virus taxonomy—Eighth report of the international committee on taxonomy of viruses*, eds Fauquet C M, Mayo M A, Maniloff J, Desselberger U, & Ball L A (Academic Press, San Diego), pp 873-883.
33. Delmas B, et al. (2005) Birnaviridae. *Virus taxonomy—Eighth report of the international committee on taxonomy* of viruses, eds Fauquet C M, Mayo M A, Maniloff J, Desselberger U, & Ball L A (Academic Press, San Diego), pp 561-569.
34. Liu C, et al. (2006) Isolation and RNA1 nucleotide sequence determination of a new insect nodavirus from Pieris rapae larvae in Wuhan city, China. *Virus Res* 120(1-2):28-35.
35. Liu C, et al. (2006) Sequence analysis of coat protein gene of Wuhan nodavirus isolated from insect. *Virus Res* 121(1):17-22.
36. Batista P J, et al. (2008) PRG-1 and 21U-RNAs interact to form the piRNA complex required for fertility in *C. elegans*. *Mol Cell* 31(1):67-78.
37. Lau N C, et al. (2009) Abundant primary piRNAs, endo-siRNAs, and microRNAs in a *Drosophila* ovary cell line. *Genome Res*.
38. Brennecke J, et al. (2007) Discrete small RNA-generating loci as master regulators of transposon activity in *Drosophila*. *Cell* 128(6):1089-1103.
39. Saito K, et al. (2009) A regulatory circuit for piwi by the large Maf gene traffic jam in *Drosophila*. *Nature* 461 (7268):1296-1299.
40. Troemel E R, Felix M A, Whiteman N K, Barriere A, & Ausubel F M (2008) Microsporidia are natural intracellular parasites of the nematode *Caenorhabditis elegans*. *PLoS Biol* 6(12):2736-2752.
41. Kreuze J F, et al. (2009) Complete viral genome sequence and discovery of novel viruses by deep sequencing of small RNAs: a generic method for diagnosis, discovery and sequencing of viruses. *Virology* 388(1):1-7.
42. Culley A I, Lang A S, & Suttle C A (2006) Metagenomic analysis of coastal RNA virus communities. *Science* 312 (5781):1795-1798.
43. Victoria J G, Kapoor A, Dupuis K, Schnurr D P, & Delwart E L (2008) Rapid identification of known and new RNA viruses from animal tissues. *PLoS Pathog* 4(9):e1000163.
44. Cox-Foster D L, et al. (2007) A metagenomic survey of microbes in honey bee colony collapse disorder. *Science* 318(5848):283-287.
45. Mi S, et al. (2008) Sorting of small RNAs into *Arabidopsis argonaute* complexes is directed by the 5' terminal nucleotide. *Cell* 133(1):116-127.
46. Wu Q, et al. (2008) Poly A-transcripts expressed in HeLa cells. *PLoS One* 3(7):e2803.

A number of embodiments of the disclosure have been described. Nevertheless, it will be understood that various modifications may be made without departing from the spirit and scope of the disclosure. Accordingly, other embodiments are within the scope of the following claims.

What is claimed is:
1. A method for identifying a virus by identifying a viral nucleic acid in a cell, comprising:
   (a) obtaining from the cell a plurality of PIWI protein-interacting RNAs (piRNAs) of between 24 and 30 nt in length;
   (b) sequencing the plurality of piRNAs of (a);
   (c) assembling the sequences of the plurality of piRNAs into at least one contig, and determining the sequence of the at least one assembled contig;
   (d) searching a database of viral sequences comprising a viral genome, viral nucleic acid or viral protein encoding sequence, or subsequence thereof against the sequence of the at least one assembled contig to determine if the database of viral sequences does, or does not, have a significant homology to a sequence of the at least one assembled contig,
   wherein the viral genome, viral nucleic acid or viral protein encoding sequence, or subsequence thereof, has a significant homology to the at least one assembled contig when it has at least about 50% to 100% homology to the at least one assembled contig;
   and wherein determining that a viral genome, viral nucleic acid or viral protein encoding sequence, or subsequence thereof, has a significant homology to the at least one assembled contig identifies the at least one assembled contig as comprising a viral genome, a viral nucleic acid or a viral protein encoding sequence, or a subsequence thereof, in the cell, thereby identifying a virus in the cell.
2. The method of claim 1, wherein the cell is from a vertebrate, an invertebrate, an insect (*Anthropoda*), a nematode (*Nemapoda*), a *Mollusca*, a *Porifera*, a plant, a fungi, an algae, or a *Cyanobacteria*.
3. The method of claim 1, wherein the cell is from an organism or organisms from an environmental sample.
4. The method of claim 3, wherein the environmental sample is a soil sample, a water sample or an air sample.
5. The method of claim 1, wherein the sequences of the plurality of PIWI-interacting RNAs (piRNAs) are assembled into at least two contigs, and the method further comprises filling in gaps between at least two contigs that have a significant homology to the viral genome, viral nucleic acid or viral protein encoding sequence, or subsequence thereof.
6. The method of claim 5, wherein filling in gaps between the at least two contigs comprises using RT-PCR, sequencing or RT-PCR and sequencing.
7. The method of claim 1, wherein the database of viral sequences comprises non-redundant nucleotide sequences.

SEQUENCE LISTING

```
<160> NUMBER OF SEQ ID NOS: 1

<210> SEQ ID NO 1
<211> LENGTH: 18
<212> TYPE: DNA
<213> ORGANISM: artificial
<220> FEATURE:
<223> OTHER INFORMATION: 3' adaptor sequence

<400> SEQUENCE: 1
acactcgggc accaagga                                                 18
```

8. The method of claim 1, further comprises translating the sequence of the at least one assembled contig in silico, and determining whether the translated sequence has a significant homology to a known protein sequence in a viral protein database.

9. The method of claim 1, further comprising making a phylogenetic analysis of the at least one assembled contig sequence that has significant homology to a viral genome, a viral nucleic acid or a viral protein encoding sequence, or a subsequence thereof.

10. The method of claim 9, further comprising identifying and annotating the phylogenetic analysis.

11. The method of claim 1, wherein the obtaining from the cell the plurality of piRNAs comprises substantially purifying or isolating the piRNAs before the sequencing.

12. The method of claim 1, further comprising assembling into a library the plurality of piRNAs.

13. The method of claim 1, further comprising amplifying a contig sequence identified as a viral genome, a viral nucleic acid or a viral protein encoding sequence, or a subsequence thereof, using a Rapid Amplification of cDNA Ends (RACE) process, to generate a sequence of an RNA transcript found within the cell.

14. The method of claim 13, wherein the RACE is a 5'-RACE, a 3'-RACE or a 5'-RACE and a 3'-RACE.

15. The method of claim 13, further comprising sequencing the RACE-amplified sequences.

\* \* \* \* \*